United States Patent
Shi

(10) Patent No.: US 9,808,558 B2
(45) Date of Patent: *Nov. 7, 2017

(54) ALLOGRAFTS COMBINED WITH TISSUE DERIVED STEM CELLS FOR BONE HEALING

(71) Applicant: AlloSource, Centennial, CO (US)

(72) Inventor: Yaling Shi, Larkspur, CO (US)

(73) Assignee: AlloSource, Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/880,675

(22) Filed: Oct. 12, 2015

(65) Prior Publication Data

US 2016/0045640 A1    Feb. 18, 2016

Related U.S. Application Data

(63) Continuation of application No. 12/612,583, filed on Nov. 4, 2009, now Pat. No. 9,192,695.

(60) Provisional application No. 61/116,484, filed on Nov. 20, 2008.

(51) Int. Cl.

| | |
|---|---|
| A61K 35/38 | (2015.01) |
| A61L 27/38 | (2006.01) |
| A61L 27/36 | (2006.01) |
| A61L 27/54 | (2006.01) |
| C12N 5/0775 | (2010.01) |
| A01N 1/02 | (2006.01) |
| A61K 35/12 | (2015.01) |

(52) U.S. Cl.

CPC .......... *A61L 27/3834* (2013.01); *A01N 1/021* (2013.01); *A61K 35/38* (2013.01); *A61L 27/3608* (2013.01); *A61L 27/3847* (2013.01); *A61L 27/3895* (2013.01); *A61L 27/54* (2013.01); *C12N 5/0662* (2013.01); *C12N 5/0667* (2013.01); *A61K 35/12* (2013.01); *A61L 2300/406* (2013.01); *A61L 2430/02* (2013.01); *C12N 2509/00* (2013.01); *C12N 2533/18* (2013.01); *C12N 2533/90* (2013.01)

(58) Field of Classification Search
None
See application file for complete search history.

(56) References Cited

U.S. PATENT DOCUMENTS

| | | |
|---|---|---|
| 4,627,853 A | 12/1986 | Campbell et al. |
| 5,073,373 A | 12/1991 | O'Leary et al. |
| 5,197,985 A | 3/1993 | Caplan et al. |
| 5,284,655 A | 2/1994 | Bogdansky et al. |
| 5,298,254 A | 3/1994 | Prewett et al. |
| 5,306,304 A | 4/1994 | Gendler |
| 5,314,476 A | 5/1994 | Prewett et al. |
| 5,405,390 A | 4/1995 | O'Leary et al. |
| 5,439,684 A | 8/1995 | Prewett et al. |
| 5,486,359 A | 1/1996 | Caplan |
| 5,507,813 A | 4/1996 | Dowd et al. |
| 5,510,396 A | 4/1996 | Prewett et al. |
| 5,516,532 A | 5/1996 | Atala et al. |
| 5,531,791 A | 7/1996 | Wolfinbarger |
| 5,556,379 A | 9/1996 | Wolfinbarger |
| 5,676,146 A | 10/1997 | Scarborough |
| 5,707,962 A | 1/1998 | Chen et al. |
| 5,736,396 A | 4/1998 | Bruder et al. |
| 5,749,874 A | 5/1998 | Schwartz |
| 5,769,899 A | 6/1998 | Schwartz et al. |
| 5,786,207 A | 7/1998 | Katz et al. |
| 5,788,941 A | 8/1998 | Dalmasso et al. |
| 5,797,871 A | 8/1998 | Wolfinbarger |
| 5,811,094 A | 9/1998 | Caplan |
| 5,820,581 A | 10/1998 | Wolfinbarger |
| 5,827,740 A | 10/1998 | Pittenger |

(Continued)

FOREIGN PATENT DOCUMENTS

| | | |
|---|---|---|
| WO | 9726326 | 7/1997 |
| WO | 0200272 A2 | 1/2002 |

(Continued)

OTHER PUBLICATIONS

Yin et al., Vitreous cryopreservation of tissue engineered bone composed of bone marrow mesenchymal stem cells and partially demineralized bone matrix, Cryobiology, vol. 59 (2009), pp. 180-187.*
Ahn, et al., "In Vivo Osteogenic Differentiation of Human Adipose-Derived Stem Cells in an Injectable in Situ-Forming D Gel Scaffold", Tissue Eng Part A, 2009, vol. 15, No. 7, pp. 1821-1832.
Angelo, "Micronutrients and Bone Health", Linus Pauling Institute, [accessed on Oct. 20, 2015, retrieved from the Internet: <http://lpi.oregonstate.edu/infocenter/bonehealth.html>].
Anghileri, et al., "Neuronal Differentiation Potential of Human Adipose-Derived Mesenchymal Stem Cells", Stem Cells Dev., 2008, vol. 17, No. 5, pp. 909-916.
Arnalich-Montiel, et al., "Adipose-Derived Stem Cells Are a Source for Cell Therapy of the Corneal Stroma", Stem Cells, 2008, vol. 26, pp. 570-579.

(Continued)

*Primary Examiner* — Thane Underdahl
*Assistant Examiner* — Yvonne Pyla
(74) *Attorney, Agent, or Firm* — Kilpatrick Townsend & Stockton LLP

(57) ABSTRACT

There is disclosed a method of combining mesenchymal stem cells (MSCs) with a bone substrate. In an embodiment, the method includes obtaining tissue having MSCs together with unwanted cells. The tissue is digested to form a cell suspension having MSCs and unwanted cells. The cell suspension is added to the substrate. The substrate is cultured to allow the MSCs to adhere. The substrate is rinsed to remove unwanted cells. In various embodiments, the tissue is adipose tissue, muscle tissue, or bone marrow tissue. In an embodiment, there is disclosed an allograft product including a combination of MSCs with a bone substrate in which the combination is manufactured by culturing MSCs disposed on the substrate for a period of time to allow the MSCs to adhere to the substrate, and then rinsing the substrate to remove unwanted cells from the substrate. Other embodiments are also disclosed.

24 Claims, 6 Drawing Sheets

(56) References Cited

U.S. PATENT DOCUMENTS

| | | |
|---|---|---|
| 5,895,426 A | 4/1999 | Scarborough et al. |
| 5,899,939 A | 5/1999 | Boyce et al. |
| 5,906,934 A | 5/1999 | Grande et al. |
| 5,908,782 A | 6/1999 | Marshak et al. |
| 5,908,784 A | 6/1999 | Johnstone et al. |
| 5,942,225 A | 8/1999 | Bruder et al. |
| 5,948,428 A | 9/1999 | Lee et al. |
| 5,962,325 A | 10/1999 | Naughton et al. |
| 5,972,368 A | 10/1999 | McKay |
| 5,976,104 A | 11/1999 | Wolfinbarger |
| 5,977,034 A | 11/1999 | Wolfinbarger |
| 5,977,432 A | 11/1999 | Wolfinbarger |
| 6,022,540 A | 2/2000 | Bruder et al. |
| 6,024,735 A | 2/2000 | Wolfinbarger |
| 6,030,635 A | 2/2000 | Gertzman et al. |
| 6,030,836 A | 2/2000 | Thiede |
| 6,090,998 A | 7/2000 | Grooms et al. |
| 6,143,012 A | 11/2000 | Gausepohl |
| 6,174,333 B1 | 1/2001 | Kadiyala |
| 6,180,606 B1 | 1/2001 | Chen et al. |
| 6,189,537 B1 | 2/2001 | Wolfinbarger |
| 6,200,347 B1 | 3/2001 | Anderson et al. |
| 6,200,606 B1 | 3/2001 | Peterson |
| 6,214,369 B1 | 4/2001 | Grande |
| 6,225,119 B1 | 5/2001 | Qasba et al. |
| 6,235,316 B1 | 5/2001 | Adkisson |
| 6,291,240 B1 | 9/2001 | Mansbridge et al. |
| 6,294,041 B1 | 9/2001 | Boyce et al. |
| 6,294,187 B1 | 9/2001 | Boyce et al. |
| 6,305,379 B1 | 10/2001 | Wolfinbarger |
| 6,315,795 B1 | 11/2001 | Scarborough et al. |
| 6,322,784 B1 | 11/2001 | Pittenger et al. |
| 6,326,018 B1 | 12/2001 | Gertzman et al. |
| 6,340,477 B1 | 1/2002 | Anderson |
| 6,355,239 B1 | 3/2002 | Bruder |
| 6,371,988 B1 | 4/2002 | Pafford et al. |
| 6,379,953 B1 | 4/2002 | Bruder et al. |
| 6,387,367 B1 | 5/2002 | Davis-Sproul et al. |
| 6,391,297 B1 | 5/2002 | Halvorsen |
| 6,436,138 B1 | 8/2002 | Dowd |
| 6,464,983 B1 | 10/2002 | Grotendorst |
| 6,478,825 B1 | 11/2002 | Winterbottom et al. |
| 6,482,231 B1 | 11/2002 | Abatangelo |
| 6,482,233 B1 | 11/2002 | Aebi et al. |
| 6,511,509 B1 | 1/2003 | Ford et al. |
| 6,534,095 B1 | 3/2003 | Moore-Smith et al. |
| 6,541,024 B1 | 4/2003 | Kadiyala et al. |
| 6,555,374 B1 | 4/2003 | Gimble et al. |
| 6,576,015 B2 | 6/2003 | Geistlich et al. |
| 6,616,698 B2 | 9/2003 | Scarborough |
| 6,645,764 B1 | 11/2003 | Adkisson |
| 6,652,593 B2 | 11/2003 | Boyer, II et al. |
| 6,685,626 B2 | 2/2004 | Wironen |
| 6,696,073 B2 | 2/2004 | Boyce et al. |
| 6,716,245 B2 | 4/2004 | Pasquet et al. |
| 6,746,484 B1 | 6/2004 | Liu et al. |
| 6,777,231 B1 | 8/2004 | Katz |
| 6,800,480 B1 | 10/2004 | Bodnar et al. |
| 6,805,713 B1 | 10/2004 | Carter et al. |
| 6,808,585 B2 | 10/2004 | Boyce et al. |
| 6,835,377 B2 | 12/2004 | Goldberg et al. |
| 6,837,907 B2 | 1/2005 | Wolfinbarger |
| 6,855,169 B2 | 2/2005 | Boyer et al. |
| 6,863,694 B1 | 3/2005 | Boyce et al. |
| 6,863,900 B2 | 3/2005 | Kadiyala |
| 6,902,578 B1 | 6/2005 | Anderson et al. |
| 6,911,045 B2 | 6/2005 | Shimp |
| 6,911,212 B2 | 6/2005 | Gertzman et al. |
| 6,989,030 B1 | 1/2006 | Ohgushi |
| 6,998,135 B1 | 2/2006 | Sunwoo et al. |
| 7,018,412 B2 | 3/2006 | Ferreira et al. |
| 7,029,666 B2 | 4/2006 | Bruder et al. |
| 7,048,765 B1 | 5/2006 | Grooms et al. |
| 7,115,146 B2 | 10/2006 | Boyer, II et al. |
| 7,132,110 B2 | 11/2006 | Kay et al. |
| 7,153,500 B2 | 12/2006 | Qasba et al. |
| 7,163,691 B2 | 1/2007 | Knaack et al. |
| 7,172,629 B2 | 2/2007 | McKay |
| 7,179,649 B2 | 2/2007 | Halvorsen |
| 7,241,874 B2 | 7/2007 | Thorne |
| 7,259,011 B2 | 8/2007 | Lucas |
| 7,291,450 B2 | 11/2007 | Sowemimo-Coker et al. |
| 7,297,540 B2 | 11/2007 | Mitrani |
| 7,316,822 B2 | 1/2008 | Binette et al. |
| 7,323,011 B2 | 1/2008 | Shepard et al. |
| 7,335,381 B2 | 2/2008 | Malinin |
| 7,338,517 B2 | 3/2008 | Yost et al. |
| 7,361,195 B2 | 4/2008 | Schwartz et al. |
| 7,371,409 B2 | 5/2008 | Petersen et al. |
| 7,470,537 B2 | 12/2008 | Hedrick et al. |
| 7,473,420 B2 | 1/2009 | Fraser et al. |
| 7,498,040 B2 | 3/2009 | Masinaei et al. |
| 7,501,115 B2 | 3/2009 | Fraser et al. |
| 7,582,309 B2 | 9/2009 | Rosenberg et al. |
| 7,595,043 B2 | 9/2009 | Hedrick et al. |
| 7,608,113 B2 | 10/2009 | Boyer et al. |
| 7,622,562 B2 | 11/2009 | Thorne et al. |
| 7,625,581 B2 | 12/2009 | Laredo et al. |
| 7,662,185 B2 | 2/2010 | Alfaro et al. |
| 7,662,625 B2 | 2/2010 | Stern et al. |
| 7,687,059 B2 | 3/2010 | Fraser et al. |
| 7,732,126 B2 | 6/2010 | Zhang et al. |
| 7,753,963 B2 | 7/2010 | Boyer et al. |
| 7,763,071 B2 | 7/2010 | Bianchi et al. |
| 7,776,089 B2 | 8/2010 | Bianchi et al. |
| 7,785,634 B2 | 8/2010 | Borden |
| 7,807,458 B2 | 10/2010 | Schiller |
| 7,811,608 B2 | 10/2010 | Kay et al. |
| 7,815,926 B2 | 10/2010 | Syring et al. |
| 7,837,740 B2 | 11/2010 | Semler et al. |
| 7,863,043 B2 | 1/2011 | Gentry et al. |
| 7,875,296 B2 | 1/2011 | Binette et al. |
| 7,879,103 B2 | 2/2011 | Gertzman et al. |
| 7,883,511 B2 | 2/2011 | Fernyhough |
| RE42,208 E | 3/2011 | Truncale et al. |
| 7,914,779 B2 | 3/2011 | Hariri |
| 7,931,692 B2 | 4/2011 | Sybert et al. |
| 8,002,813 B2 | 8/2011 | Scarborough et al. |
| 8,002,837 B2 | 8/2011 | Stream et al. |
| 8,021,692 B2 | 9/2011 | Hiles |
| 8,025,896 B2 | 9/2011 | Malaviya et al. |
| 8,039,016 B2 | 10/2011 | Drapeau et al. |
| RE43,258 E | 3/2012 | Truncale et al. |
| 8,133,421 B2 | 3/2012 | Boyce et al. |
| 8,137,702 B2 | 3/2012 | Binette et al. |
| 8,163,549 B2 | 4/2012 | Yao et al. |
| 8,167,943 B2 | 5/2012 | Carter et al. |
| 8,197,474 B2 | 6/2012 | Scarborough et al. |
| 8,202,539 B2 | 6/2012 | Behnam et al. |
| 8,221,500 B2 | 7/2012 | Truncale et al. |
| 8,268,008 B2 | 9/2012 | Betz et al. |
| 8,292,968 B2 | 10/2012 | Truncale et al. |
| 8,328,876 B2 | 12/2012 | Behnam et al. |
| 8,334,135 B2 | 12/2012 | Rodriguez et al. |
| 8,343,229 B2 | 1/2013 | Coale |
| 8,357,384 B2 | 1/2013 | Behnam et al. |
| 8,389,017 B1 | 3/2013 | Starling et al. |
| 8,399,010 B2 | 3/2013 | McKay |
| 8,403,991 B2 | 3/2013 | Ullrich, Jr. et al. |
| 8,409,623 B2 | 4/2013 | Shim et al. |
| 8,435,566 B2 | 5/2013 | Behnam et al. |
| 8,496,970 B2 | 7/2013 | Binette et al. |
| 8,506,632 B2 | 8/2013 | Ganem et al. |
| 8,551,176 B2 | 10/2013 | Ullrich, Jr. et al. |
| 8,563,040 B2 | 10/2013 | Marchosky |
| 8,574,825 B2 | 11/2013 | Shelby et al. |
| 8,585,766 B2 | 11/2013 | Ullrich, Jr. et al. |
| 8,637,004 B2 | 1/2014 | Danilkovich et al. |
| 8,652,214 B2 | 2/2014 | Fritz et al. |
| 8,652,458 B2 | 2/2014 | Jackson et al. |
| 8,722,075 B2 | 5/2014 | Shimp et al. |
| 8,734,525 B2 | 5/2014 | Behnam et al. |
| 8,758,791 B2 | 6/2014 | McKay |
| 8,771,368 B2 | 7/2014 | McKay |

(56) References Cited

U.S. PATENT DOCUMENTS

| | | |
|---|---|---|
| 8,834,928 B1 | 9/2014 | Truncale et al. |
| 8,859,007 B2 | 10/2014 | Carter et al. |
| 8,865,199 B2 | 10/2014 | Coleman et al. |
| 8,883,210 B1 | 11/2014 | Truncale et al. |
| 8,945,535 B2 | 2/2015 | Steinwachs et al. |
| 8,992,964 B2 | 3/2015 | Shelby et al. |
| 9,029,077 B2 | 5/2015 | Song et al. |
| 9,050,178 B2 | 6/2015 | Barry et al. |
| 9,095,524 B2 | 8/2015 | Warnke et al. |
| 9,162,012 B2 | 10/2015 | Benham et al. |
| 9,180,166 B2 | 11/2015 | Arinzeh et al. |
| 9,192,695 B2 | 11/2015 | Shi |
| 9,193,948 B2 | 11/2015 | Nicoll et al. |
| 2002/0192263 A1 | 12/2002 | Merboth et al. |
| 2003/0050709 A1 | 3/2003 | Noth et al. |
| 2003/0161817 A1 | 8/2003 | Young et al. |
| 2004/0043006 A1 | 3/2004 | Badylak et al. |
| 2004/0078090 A1 | 4/2004 | Binette et al. |
| 2005/0048036 A1 | 3/2005 | Hedrick et al. |
| 2006/0134781 A1 | 6/2006 | Yang et al. |
| 2006/0210643 A1 | 9/2006 | Truncale et al. |
| 2007/0014729 A1 | 1/2007 | Farhat et al. |
| 2007/0020248 A1 | 1/2007 | Everaerts et al. |
| 2007/0134216 A1 | 6/2007 | Harlow et al. |
| 2007/0179607 A1 | 8/2007 | Hodorek et al. |
| 2007/0185231 A1 | 8/2007 | Liu et al. |
| 2007/0212676 A1 | 9/2007 | Takakura |
| 2007/0249044 A1 | 10/2007 | Desai et al. |
| 2007/0258963 A1 | 11/2007 | Danilkovitch et al. |
| 2007/0265705 A1 | 11/2007 | Gaissmaier et al. |
| 2008/0058953 A1 | 3/2008 | Scarborough |
| 2008/0249632 A1 | 10/2008 | Stone et al. |
| 2008/0249638 A1 | 10/2008 | Asgari |
| 2008/0269895 A1 | 10/2008 | Steinwachs et al. |
| 2008/0286268 A1 | 11/2008 | Johnson |
| 2008/0305145 A1 | 12/2008 | Shelby et al. |
| 2008/0306610 A1 | 12/2008 | Wang et al. |
| 2009/0024223 A1 | 1/2009 | Chen et al. |
| 2009/0041730 A1 | 2/2009 | Barry et al. |
| 2009/0053279 A1 | 2/2009 | Badylak et al. |
| 2009/0202977 A1 | 8/2009 | Ott et al. |
| 2010/0049322 A1 | 2/2010 | McKay |
| 2010/0124776 A1 | 5/2010 | Shi |
| 2010/0168869 A1 | 7/2010 | Long et al. |
| 2010/0196333 A1 | 8/2010 | Gaskins et al. |
| 2010/0241228 A1 | 9/2010 | Syring et al. |
| 2010/0247494 A1 | 9/2010 | Gregory et al. |
| 2011/0045044 A1 | 2/2011 | Masinaei et al. |
| 2011/0070271 A1 | 3/2011 | Truncale et al. |
| 2011/0182961 A1 | 7/2011 | McKay |
| 2011/0262404 A1 | 10/2011 | Badoer et al. |
| 2011/0262516 A1 | 10/2011 | Zheng et al. |
| 2011/0293577 A1 | 12/2011 | Vesey |
| 2011/0311496 A1 | 12/2011 | Pittenger et al. |
| 2011/0318314 A1 | 12/2011 | Aggarwal et al. |
| 2012/0035276 A1 | 2/2012 | Spievack |
| 2012/0082704 A1 | 4/2012 | Phillips et al. |
| 2012/0087958 A1 | 4/2012 | Dufrane et al. |
| 2012/0148537 A1 | 6/2012 | Chan et al. |
| 2012/0148548 A1 | 6/2012 | Barry et al. |
| 2012/0189707 A1 | 7/2012 | Chun et al. |
| 2012/0213859 A1 | 8/2012 | Shelby et al. |
| 2012/0251609 A1 | 10/2012 | Huang et al. |
| 2012/0259415 A1 | 10/2012 | Van Dyke et al. |
| 2012/0297550 A1 | 11/2012 | Ngo et al. |
| 2012/0308529 A1 | 12/2012 | Zanotti et al. |
| 2013/0004464 A1 | 1/2013 | Nadal-Ginard |
| 2013/0013068 A1 | 1/2013 | Forsell et al. |
| 2013/0122095 A1 | 5/2013 | Kestler et al. |
| 2013/0131804 A1 | 5/2013 | Barry et al. |
| 2013/0149294 A1 | 6/2013 | Rueger et al. |
| 2013/0189338 A1 | 7/2013 | Drapeau et al. |
| 2013/0195809 A1 | 8/2013 | Crawford et al. |
| 2013/0195810 A1 | 8/2013 | Crawford et al. |
| 2013/0197654 A1 | 8/2013 | Samuelson et al. |
| 2013/0316454 A1 | 11/2013 | Lu et al. |
| 2014/0024115 A1 | 1/2014 | Bogdansky et al. |
| 2014/0037598 A1 | 1/2014 | Jansen et al. |
| 2014/0093543 A1 | 4/2014 | Morreale |
| 2014/0105872 A1 | 4/2014 | Danilkovich et al. |
| 2014/0112894 A1 | 4/2014 | Zheng et al. |
| 2014/0121772 A1 | 5/2014 | Emerton et al. |
| 2014/0127177 A1 | 5/2014 | Tom et al. |
| 2014/0161776 A1 | 6/2014 | Aggarwal et al. |
| 2014/0170232 A1 | 6/2014 | Shelby et al. |
| 2014/0205674 A1 | 7/2014 | Wei |
| 2014/0208980 A1 | 7/2014 | Song et al. |
| 2014/0212471 A1 | 7/2014 | Drapeau et al. |
| 2014/0212499 A1 | 7/2014 | Cooper et al. |
| 2014/0220142 A1 | 8/2014 | Song et al. |
| 2014/0227339 A1 | 8/2014 | Jackson et al. |
| 2014/0234272 A1 | 8/2014 | Vesey et al. |
| 2014/0255356 A1 | 9/2014 | Victor et al. |
| 2014/0255506 A1 | 9/2014 | Behnam et al. |
| 2014/0277570 A1 | 9/2014 | Behnam et al. |
| 2014/0286911 A1 | 9/2014 | Shi et al. |
| 2014/0314822 A1 | 10/2014 | Carter et al. |
| 2014/0342013 A1 | 11/2014 | He et al. |
| 2015/0004247 A1 | 1/2015 | Carter et al. |
| 2015/0010506 A1 | 1/2015 | Jansen et al. |
| 2015/0012107 A1 | 1/2015 | Koford et al. |
| 2015/0030571 A1 | 1/2015 | Tremolada |
| 2015/0037387 A1 | 2/2015 | Coleman et al. |
| 2015/0093429 A1 | 4/2015 | Carter et al. |
| 2015/0174295 A1 | 6/2015 | Woodell-May et al. |
| 2015/0182667 A1 | 7/2015 | Guelcher et al. |
| 2015/0202345 A1 | 7/2015 | Shelby et al. |
| 2015/0202346 A1 | 7/2015 | Shelby et al. |
| 2015/0251361 A1 | 9/2015 | Meyer et al. |
| 2015/0258244 A1 | 9/2015 | Shelby et al. |
| 2015/0306278 A1 | 10/2015 | McKay |
| 2016/0030639 A1 | 2/2016 | Shi |
| 2016/0067377 A1 | 3/2016 | Shi et al. |
| 2016/0144076 A1 | 5/2016 | Matheny et al. |
| 2016/0263284 A1 | 9/2016 | Shi |

FOREIGN PATENT DOCUMENTS

| | | |
|---|---|---|
| WO | 2006062989 A1 | 6/2006 |
| WO | 2006112390 A1 | 10/2006 |
| WO | 2008036374 A2 | 3/2008 |
| WO | 2008041854 A1 | 4/2010 |
| WO | 2010059565 | 5/2010 |
| WO | 2012135205 | 10/2012 |
| WO | 2013047936 | 4/2013 |
| WO | 2015053739 A1 | 4/2015 |

OTHER PUBLICATIONS

Aubin, et al., Isolation of Bone Cell Clones with Differences in Growth, Hormone Responses, and Extracellular Matrix Production, 92 J. Cell. Biol. 452-61 (1982).

Baer, et al., "Adipose-Derived Mesenchymal Stromal/Stem Cells: Tissue Localization, Characterization, and Heterogeneity," Stem Cells International, Hidsawi Publishing, vol. 2012, Article ID 812693, 11 pages.

Barry, , "Mesenchymal stem cell therapy in joint disease," Tissue engineering of cartilage and bone: Novartis Foundation Symposium, 249, 86-102 (2003).

Bennett, et al., Adipocytic cells cultured from marrow have osteogenic potential, 99 J. Cell. Sci. 131 (1991).

Bruder, et al., "Tissue Engineering of Bone. Cell Based Strategies", Clin Orthop Relat Res., 1999, vol. 367 Suppl., pp. S68-S83.

Bunnell, et al., "Adipose-Derived Stem Cells: Isolation, Expansion and Differentiation", Methods, 2008, vol. 45, No. 2, pp. 115-120.

Butt, et al., "Stimulation of Peri-Implant Vascularization with Bone Marrow-Derived Progenitor Cells: Monitoring by in Vivo EPR Oximetry", Tissue Eng., 2007, vol. 13, No. 8, pp. 2053-2061.

Cha, et al., "Stem cells in cutaneous wound healing," Clinics in Dermatology 25:73-78 (2007).

Chamberlain, et al., "Concise Review: Mesenchymal Stem Cells: Their Phenotype, Differentiation Capacity, Immunological Features, and Potential for Homing," Stem Cells (2007) 25:2739-2749.

(56) References Cited

OTHER PUBLICATIONS

Chen, et al., "Differentiation of Rat Adipose-Derived Stem Cells into Smooth-Muscle-Like Cells in Vitro", Zhonghua Nan Ke Xue, 2009, vol. 15, No. 5, pp. 425-430.
Chen, et al., "Study of MSCs in Vitro Cultured on Demineralized Bone Matrix of Mongrel", Shanghai Kou Qiang Yi Xue, 2007, vol. 16, No. 3, pp. 255-258.
Cheng, et al., "Chondrogenic Differentiation of Adipose-Derived Adult Stem Cells by a Porous Scaffold Derived from Native Articular Cartilage Extracellular Matrix", Tissue Eng Part A, 2009, vol. 15, No. 2, pp. 231-241.
Chu, et al. "Leukocytes in blood transfusion: adverse effects and their prevention," HKMJ (1999) 5:280-284.
Chung, et al., "Bladder Reconstitution with Bone Marrow Derived Stem Cells Seeded on Small Intestinal Submucosa Improves Morphological and Molecular Composition," J. Urology 174:353-359 (2005).
Cui, et al., "Repair of Cranial Bone Defects with Adipose Derived Stem Cells and Coral Scaffold in a Canine Model", Biomaterials, 2007, vol. 28, pp. 5477-5486.
Damien, et al., "Bone Graft and Bone Graft Substitutes: A Review of Current Technology and Applications", Journal Applied Biomaterials, 1991, vol. 2, pp. 187-208.
De Girolamo, et al., "Human Adipose-Derived Stem Cells as Future Tools in Tissue Regeneration: Ostegenic Differentiation and Cell-Scaffold Interaction", Int J Artif Organs, 2008, vol. 31, No. 6, pp. 467-479.
De Girolamo, et al. "Osteogenic Differentiation of Human Adipose-Derived Stem Cells: Comparison of Two Different Inductive Media", J Tissue Eng Regen Med, 2007, vol. 1, No. 2, pp. 154-157.
De Long, et al., "Bone Grafts and Bone Graft Substitutes in Orthpaedic Trauma Surgery. A Critical Analysis", The Journal of Bone & Joint Surgery, 2007, vol. 89, pp. 649-658.
De Ugarte, et al., "Comparison of Multi-Lineage Cells from Human Adipose Tissue and Bone Marrow", Cells Tissues Organs, 2003, vol. 174, No. 3, pp. 101-109.
Diekman, et al., "Chondrogenesis of adult stem cells from adipose tissue and bone marrow: Induction by growth factors and cartilage-derived matrix," Tissue Engineering, 16, 523-533 (2010); pub. online Sep. 2009.
Di Bella, et al., "Bone Regeneration in a Rabbit Critical-Sized Skull Defect Using Autologous Adipose-Derived Cells", Tissue Eng Part A., 2008, vol. 14, No. 4, pp. 483-490.
Dubois, et al., Methods in Molecular Biology, vol. 449, 2008, pp. 69-79.
Elabd, et al., "Human Adipose Tissue-Derived Multipotent Stem Cells Differentiate in Vitro and in Vivo into Ostecyte-Like Cells", Biochem Biophys Res Commun., 2007, vol. 361, No. 2, pp. 342-348.
Eyre, D. Collagen of articular cartilage, Arthritis Res. 4:30-35 (2002).
Filipak, Michiko et al., Tumor Necrosis Factor Inhibits the Terminal Event in Mesenchymal Stem Cell Differentiation, 137, J. Cell. Phys. 368, 367-73 (1988).
Flynn, L., et al., "Adipose Tissue Engineering With Naturally Derived Scaffolds and Adipose-Derived Stem Cells", Biomaterials, 2007, vol. 28, No. 26, pp. 3834-3842.
Flynn, L., et al., "Proliferation and Differentiation of Adipose-Derived Stem Cells on Naturally Derived Scaffolds", Biomaterials, 2008, vol. 29, No. 12, pp. 1862-1871.
Fraser, JK, et al., "Adipose-Derived Stem Cells", Methods Mol Bioi., 2008, vol. 449, pp. 59-67.
Freed, L.E. et al., Joint resurfacing using allograft chondrocytes and synthetic biodegradable polymer scaffolds, 28 J. Biomed. Mater. Res. 891 (1994).
Gamradt, et al., "Bone Graft for Revision Hip Arthroplasty: Biology and Future Applications", Clin Orthop Relat D Res., 2003, vol. 417, pp. 183-194.

Gimble, et al., "Differentiation Potential of Adipose Derived Adult Stem (ADAS) Cells", Curr Top Dev Bioi., 2003, vol. 58, pp. 137-160.
Gimble, J., et al., "Adipose-Derived Adult Stem Cells: Isolation, Characterization, and Differentiation Potential", Cytotherapy, 2003, vol. 5, No. 5, pp. 362-369.
Glowacki, et al., "Application of the Biological Principle of Induced Osteogenesis for Craniofacial Defects", The Lancet, 1981, pp. 959-962.
Goh, et al., "Cryopreservation Characteristics of Adipose Derived Stem Cells: Maintenance of 6 Differentiation Potential and Viability", Journal of Tissue Engineering and Regenerative Medicine, 2007, vol. 1, pp. 322-324.
Gomes, et al., "Tissue Engineering: Key Elements and Some Trends", Macromolecular Bioscience, 2004, vol. 4, pp. 737-742.
Greenwald, et al., "Bone-Graft Substitutes: Facts, Fictions, and Applications", The Journal of Bone & Joint Surgery, 2001, vol. 83, pp. 98-103.
Grewal, et al., "BMP-2 Does Not Influence the Osteogenic Fate of Human Adipose-Derived Stem Cells", Plast Reconstr Surg., 2009, vol. 123(2 Suppl), pp. 158S-165S.
Grigoriadis, A.E. et al., Differentiation of Muscle, Fat, Cartilage, and Bone from Progenitor Cells Present in a Bone-derived Clonal Cell Population: Effect of Dexamethasone, 106, J. Cell. Biol. 2144, 2139-51 (1988).
Hayashi, et al., "Comparison of Osteogenic Ability of Rat Mesenchymal Stem Cells from Bone Marrow, Periosteum, and Adipose Tissue", CalcifTissue Int., 2008, vol. 82, No. 3, pp. 238-247.
Hicok et al., Tissue Engineering, vol. 10, No. 3/4, 2004, pp. 371-382.
Honsawek, S., et al., Effects of Demineralized Bone Matrix on Proliferation and Osteogenic Differentiation of Mesenchymal Stem Cells from Human Umbilical Cord, J Med Assoc Thai, 2006, vol. 89, Suppl 3, pp. 189-195.
Hutmacher, et al., "State of the Art and Future Directions of Scaffold-Based Bone Engineering from a Biomaterials Perspective", Journal of Tissue Engineering and Regenerative Medicine, 2007, vol. 1, pp. 245-260.
International Search Report and Written Opinion dated Jun. 29, 2010 for application No. PCT/US2009/064611, 11 pages.
International Search Report issued in connection with corresponding International Application No. PCT/US13/63674, dated Jan. 29, 2014, 9 pages.
Jin, et al., "Tissue Engineered Cartilage from hTGF beta2 Transduced Human Adipose Derived Stem Cells Seeded in PLGA/ Aiginate Compound in Vitro and in Vivo", J Biomed Mater Res A, 2008, vol. 86, No. 4, pp. 1077-1087.
Jurgens, W.J.F. et al., "Effect of tissue-harvesting site on yield of stem cells derived from adipose tissue: implications for cell-based therapies," Cell Tissue Res (2008) 332:415-426.
Kakudo, et al., "Bone Tissue Engineering Using Human Adipose-Derived Stem Cells and Honeycomb Collagen Scaffold", J Biomed Mater Res A, 2008, vol. 84, No. 1, pp. 191-197.
Kasten, P., et al., "Ectopic Bone Formation Associated With Mesenchymal Stem Cells in a Resorbably Calcium D Deficient Hydroxyapatite Carrier", Biomaterials, 2005, vol. 26, No. 29, pp. 5879-5889.
Kasten, P., et al., "Induction of Bone Tissue on Different Matrices: An In Vitro and a In Vivo Pilot Study in the SCID Mouse", Z Orthop Ihre Grenzgeb., 2004, vol. 142, No. 4, pp. 467-475.
Kim, et al., "Chondrogenic Differentiation of Adipose Tissue-Derived Mesenchymal Stem Cells: Greater Doses of Growth Factor are Necessary", J Orthop Res, 2009, vol. 27, No. 5, pp. 612-619.
Kim, et al., "Direct Comparison of Human Mesenchymal Stem Cells Derived from Adipose Tissues and Bone Marrow in Mediating Neovascularization in Response to Vascular Ischemia", Cell Physiol Biochem, 2007, vol. 20, No. 6, pp. 867-876.
Kingham, et al., "Adipose-Derived Stem Cells Differentiate into a Schwann Cell Phenotype and Promote Neurite Outgrowth in Vitro", Exp Neurol., 2007, vol. 207, No. 2, pp. 267-274.

(56) References Cited

OTHER PUBLICATIONS

Ko, et al., "In Vitro Osteogenic Differentiation of Human Mesenchymal Stem Cells and In Vivo Bone Formation in Composite Nanofiber Meshes", Tissue Eng Part A., 2008, vol. 14, No. 12, pp. 2105-2119.

Langer, et al., "Tissue Engineering", Science, 1993, vol. 260, No. 5110, pp. 920-926.

Le Blanc, K., et al., "HLA Expression and Immunologic Properties of Differentiated and Undifferentiated Mesenchymal Stem Cells", Experimented Hematology, 2003, pp. 890-896.

Lecoeur, L. et al., In vitro induction of osteogenic differentiation from non-osteogenic mesenchymal cells, 18 Biomaterials 989 (1997).

Lin, et al., "Comparison of Osteogenic Potentials of BMP4 Transduced Stem Cells from Autologous Bone Marrow and Fat Tissue in a Rabbit Model of Calvarial Defects", CalcifTissue Int., 2009, vol. 85, No. 1, pp. 55-56.

Liu, et al., "Evaluation of Partially Demineralized Osteoporotic Cancellous Bone Matrix Combined with 4 Human Bone Marrow Stromal Cells for Tissue Engineering: An In Vitro and In Vivo Study", CalcifTissue Int., 2008, vol. 83, No. 3, pp. 176-185.

Liu, et al., "Evaluation of the Viability and Osteogenic Differentiation of Cryopreserved Human Adipose-Derived Stem Cells", Cryobiology, 2008, vol. 57, pp. 18-24.

Liu, G., et al., "Tissue-Engineered Bone Formation with Cryopreserved Human Bone Marrow Mesenchymal Stem D Cells", Cryobiology, 2008, vol. 56, No. 3, pp. 209-215.

Li, et al., "Bone Regeneration by Implantation of Adipose-Derived Stromal Cells Expressing BMP-2", Biochem Biophys Res Commun, 2007, vol. 356, No. 4, pp. 836-842.

Masuno, H. et al., Synthesis of inactive nonsecretable high mannose-type lipoprotein lipase by cultured brown adipocytes of combined lipase-deficient cld/cld mice, 265 J. Biol. Chem. 1628 (1990).

Mauney, et al., "In Vitro and in Vivo Evaluation of Differentially Demineralized Cancellous Bone Scaffolds Combined with Human Bone Marrow Stromal Cells for Tissue Engineering", Biomaterials, 2005, vol. 26, pp. 3173-3185.

Melhorn, et al., "Chondrogenesis of Adipose-Derived Adult Stem Cells in a Poly-Lactide-Co-Giycolide Scaffold", 0 Tissue Eng Part A, 2009, vol. 15, No. 5, pp. 1159-1167.

Merceron, et al., "Adipose-Derived Mesenchymal Stem Cells and Biomaterials for Cartilage Tissue Engineering", Joint Bone Spine, 2008, vol. 75, No. 6, pp. 672-674.

Minana, M-D et al., "IFATS Collection: Identification of Hemangioblasts in the Adult Human Adipose Tissue," Stem Cells, 2008, 26:2696-2704.

Mischen, et al., "Metabolic and Functional Characterization of Human Adipose-Derived Stem Cells in Tissue Engineering", Plast Reconstr Surg., 2008, vol. 22, No. 3, pp. 725-738.

Mitchell, J.B., e al. "Immunophenotype of Human Adipose-Derived Cells: Temporal Changes in Stromal-Associated and Stem Cell-Associated Markers", Stem Cells, 2006, vol. 24, pp. 376-385.

Mizuno, "Adipose-Derived Stem Cells for Tissue Repair and Regeneration: Ten Years of Research and a Literature Review", J Nippon Med Sch., 2009, vol. 76, No. 2, pp. 56-66.

Mulliken, et al., "Induced Osteogenesis—The Biological Principle and Clinical Applications", Journal of Surgical Research, 1984, vol. 37, pp. 487-496.

Mulliken, et al., "Use of Demineralized Allogeneic Bone Implants for the Correction of Maxillocraniofacial Deformities", Ann Surg., 1981, vol. 194, No. 3, pp. 366-372.

Niemeyer, et al., "Comparison of Immunological Properties of Bone Marrow Stromal Cells and Adipose Tissue-Derived Stem Cells Before and After Osteogenic Differentiation in Vitro", Tissue Eng., 2007, vol. 13, No. 1, pp. 111-121.

Nih et al., "Stem Cell Basics", National Institute of Health, [accessed on Oct. 20, 2015, retrieved from the Internet: <http://stemcells.nih.gov/info/basics/pages/basics4.aspx>].

Noel, et al., "Cell Specific Differences Between Human Adipose-Derived and Mesenchymal-Stromal Cells Despite Similar Differentiation Potentials", Exp Cell Res., 2008, vol. 314, No. 7, pp. 1575-1584.

Office Action dated Apr. 10, 2013 in U.S. Appl. No. 12/965,335, 41 pages.

Pate, D.W. et al., Isolation and differentiation of mesenchymal stem cells from rabbit muscle, 44 Surg Forum 587 (1993).

Prockop, O.J., et al., "Isolation and Characterization of Rapidly Self-Renewing Stem Cells from Cultures of Human Marrow Stromal Cells", Cytotherapy, 2001, vol. 3, No. 5, pp. 393-396.

Qian, et al., "Reconstruction of Bone Using Tissue Engineering and Nanoscale Technology", Zhongguo Xiu Fu Chong Jian Wai Ke Za Zhi, 2006, vol. 20, No. 5, pp. 560-564.

Rada, et al., "Adipose Tissue-Derived Stem Cells and Their Application in Bone and Cartilage Tissue Engineering", Tissue Engineering: Part B, 2009, vol. 15, No. 2, pp. 113-125.

Reddi, "Morphogenesis and Tissue Engineering of Bone and Cartilage: Inductive Signals, Stem Cells, and Biomimetic Biomaterials", Tissue Eng., 2000, vol. 6, No. 4, pp. 351-359.

Reddi, "Role of Morphogenetic Proteins in Skeletal Tissue Engineering and Regeneration", Nat Biotechnol., 1998, vol. 16, No. 3, pp. 247-252.

Rhie, J-W. et al., "Chondrogenic differentiation of human adipose-derived stem cells in PLGA (Poly(Lactide-co-Glycolide Acid)) Scaffold," Key Engineering Materials, 342, 345-348 (2007).

Rickard, D.J., Induction of rapid osteoblast differentiation in rat bone marrow stromal cell cultures by dexamethasone and BMP-2, 161 Dev. Biol. 218 (1994).

Rigotti, et al., "Clinical Treatment of Radiotherapy Tissue Damage by Lipoaspirate Transplant: A Healing Process Mediated by Adipose-Derived Adult Stem Cells", Plast Reconstr Surg., 2007, vol. 119, No. 5, pp. 1409-1422.

Riordan, NH et al., "Non-expanded adipose stromal vascular fraction cell therapy for multiple sclerosis," Journal of Translational Medicine 2009, 7:29, 9 pages.

Sakaguchi et al., Arthritis & Rheumatism, vol. 52, No. 8, Aug. 2005, pp. 2521-2529.

Salgado, A.J. et al., "Adult Stem Cells in Bone and Cartilage Tissue Engineering,".

Singh, S. et al., "Leukocyte depletion for safe blood transfusion," Biotechnol J (2009) 4:1140-1151.

Strem, et al., "Multipotential Differentiation of Adipose Tissue-Derived Stem Cells", Keio J Med., 2005, vol. 54, No. 3, pp. 132-141.

Substrate. (n.d.). The American Heritage® Stedman's Medical Dictionary, [accessed on Oct. 20, 2015, retrieved from the Internet: <http://dictionary.reference.com/browse/substrate>.

Tapp, et al., "Adipose-Derived Stem Cells: Characterization and Current Application in Orthopaedic Tissue Repair", Exp Bioi Med (Maywood), 2008.

Tapp, et al., "Adipose-Derived Stem Cells: Characterization and Current Application in Orthpaedic Tissue Repair", Exp Bioi Med (Maywood), 2009, vol. 234, No. 1, pp. 1-9.

Tsiridis, et al., "In Vitro and In Vivo Optimization of Impaction Allografting by Demineralization and Addition of rh-OP-1", J Orthop Res, 2007, vol. 25, No. 11, pp. 1425-1437.

Van Dijk, et al., "Differentiation of Human Adipose-Derived Stem Cells Towards Cardiomyocytes is Facilitated by Laminin", Cell Tissue Res, 2008, vol. 334, No. 3, pp. 457-467.

Van, R.L. et al., Cytological and enzymological characterization of adult human adipocyte precursors in culture, 58 J. Clin. Invest. 699 (1976).

Varma, Mjo et al., "Phenotypical and Functional Characterization of Freshly Isolated Adipose Tissue-Derived Stem Cells," Stem Cells and Development, 16:91-104 (2007).

Wang, et al., "Characterization of Demineralized Bone Matrix-Induced Osteogenesis in Rat Calvarial Bone Defects: III. Gene and Protein Expression", Calcif Tissue Int., 2000, vol. 67, No. 4, pp. 314-320.

Wang, J., et al., "Characterization of Matrix-Induced Osteogenesis in Rat Calvarial Bone Defects: I. Differences in the Cellular

(56) References Cited

OTHER PUBLICATIONS

Response to Demineralized Bone Matrix Implanted in Calvarial Defects and in Subcutaneous Sites", Calcif Tissue Int., 1999, vol. 65, No. 2, pp. 156-165.
Wang, J., et al., "Characterization of Matrix-Induced Osteogenesis in Rat Calvarial Bone Defects: II. Origins of Bone-Forming Cells", CalcifTissue Int., 1999, vol. 65, No. 6, pp. 486-493.
Wei, et al., "A Novel Injectable Scaffold for Cartilage Tissue Engineering Using Adipose-Derived Adult Stem Cells", J Orthop Res., 2008, vol. 26, No. 1, pp. 27-33.
Wei, et al., "Adipose-Derived Stem Cells and Chondrogenesis", Cytotherapy, 2007, vol. 9, No. 8, pp. 712-716.
Xie, et al., "The Performance of a Bone-Derived Scaffold Material in the Repair of Critical Bone Defects in a D Rhesus Monkey Model", Biomaterials, 2007, vol. 28, No. 22, pp. 3314-3324.
Yang, Q. et al., "A cartilage ECM-derived 3-D porous acellular matrix scaffold for in vivo cartilage tissue engineering with PKH26-labeled chondrogenic bone marrow-derived mesenchymal stem cells," Biomaterials, 29, 2378-2387 (2008).
Yoo, et al., "Comparison of Immunomodulatory Properties of Mesenchymal Stem Cells Derived from Adult Human Tissues", Cell Immunol., 2009, vol. 259, No. 2, pp. 150-156.
Yoon, et al., "In Vivo Osteogenic Potential of Human Adipose-Derived Stem Cells/Poly Lactide-co-Giycolic Acid Constructs for Bone Regeneration in a Rat Critical-Sized Calvarial Defect Model", Tissue Eng., 2007, vol. 13, No. 3, pp. 619-627.
Yoshimura, et al., "Comparison of Rat Mesenchymal Stem Cells Derived from Bone Marrow, Synovium, Periosteum, Adipose Tissue, and Muscle", Cell Tissue Res., 2007, vol. 327, No. 3, pp. 449-462.
Young, H.E. et al, Pluripotent mesenchymal Stem Cells Reside within Avian Connective Tissue Matrices, 29A, In Vitro Cell. Div. Biol. 723-736 (1993).
Zhang, et al., "Adipose Tissue Engineering with Human Adipose-Derived Stem Cells and Fibrin Glue Injectable Scaffold", Zhonghua Yi Zue Za Zhi, 2008, vol. 88, No. 38, pp. 2705-2709.
Zhao, L. et al., "The study of the feasibility of segmental bone defect repair with tissue-engineered bone membrane: a qualitative observation," Strat. Traum. Limb Recon. 3:57-64 (2008).
Liu, G., et al., "Evaluation of Partially Demineralized Osteoporotic Cancellous Bone Matrix Combined with Human Bone Marrow Stromal Cells for Tissue Engineering: An In Vitro and In Vivo Study." Calcif. Tissue Int. 83(3):176-185 (Sep. 2008).
Extended European Search Report for European Patent Application No. 16183850.3, dated Sep. 27, 2016, all pages.
Finkemeier, "Bone Grafting and Bone-Graft Substitutes"; The Journal of Cone and Joint Surgery; Mar. 2002; pp. 454-464; vol. 84-A, No. 3.
Gepstein, et al. "Bridging Large Defects in Bone by Demineralized Bone Matrix in the Form of a Powder"; The Journal of Bone and Joint Surgery; Sep. 1987; pp. 984-992; vol. 69-A, No. 7.
Jeon, et al., "In Vivo Bone Formation Following Transplantation of Human Adipose-Derived Stromal Cells That Are Not Differentiated Osteogenically", Tissue Engineering Part A, vol. 14. No. 8., Aug. 2008, pp. 1285-1294.
Lovric et al., "The Effect of Processing Conditions of the Osteoinductivity of Sheep Demineralized Bone Matrix in an Ectopic Nude Rat Model: A Pilot Study", ORS 2012 Annualk Meeting, Poster No. 0629.
Mauney. et al., "Osteogenic Differentiation of Human Bone Marrow Stromal Cells on Partially Demineralized Bone Scaffolds in Vitro", Tissue Engineering, vol. 10. No. 1-2, Jan. 2004, pp. 81-92.
Pietrzak, et al., "Assay of Bone Morphogenetic Protein-2, -4, and -7 in Human Demineralized Bone Matrix", Scientific Foundation, pp. 84-90, Jun. 1972.
Reddi, et al., "Biochemical Sequences in the Transformation of Normal Fibroblasts in Adolescent Rats", Proc. Nat. Acad. Sci. USA vol. 69, No. 6, pp. 1601-1605, Jun. 1972.
Schwartz, et al. "Osteoinductivity of Demineralized Bone Matrix is Independent of Donoe Bisphosphonate Use"; The Journal of Bone and Joint Surgery; Dec. 21, 2011; pp. 2278-2286; vol. 93-A, No. 24.
Shi, et al., "Adipose-Derived Stem Cells Combined with a Demineralized Cancellous Bone Substrate for Bone Regeneration" Tissue Engineering Part A, Jun. 2012.
Shih, et al., "Restoration of bone defect and enhancement of bone ingrowth using partially demineralized bone matrix and marrow stromal cells", Journal of Orthopaedic Research, vol. 23., No. 6., Nov. 2005, pp. 1293-1299.
Urist, M., "Bone Formation by Autoinduction", *Science,* vol. 150, No. 3698, pp. 893-899. Nov. 12, 1965.
Aubin, et al., "Isolation of Bone Cell Clones with Differences in Growth, Hormone Responses, and Extracellular Matrix Production," 92 J. Cell. Biol. 452-61 (1982).
Bennett, et al., "Adipocytic cells cultured from marrow have osteogenic potential," 99 J. Cell. Sci. 131 (1991).
Notice of Allowance dated Sep. 25, 2015 for U.S. Appl. No. 12/612,583, filed Nov. 4, 2009, all pages.
International Preliminary Report on Patentability for International Application No. PCT/US2013/063674 filed Oct. 7, 2013, dated Apr. 21, 2016, 10 pages.
"Preparation of the stromal vascular fraction (SVF) from human lipaspirate" Miltenyi Biotec, 2008.
Boquest, A., et al. Neclear Reprogramming: Methods and Protocols, Chapter 4, "Isolation of Stromal Stem Cells From Human Adipose Tissue," 35-46 Humana Press, Neew Jersey, 2006.
Kroeze, R.J.; "Adipose stem cells on a biodegradable polymer for spinal fusion" Vrije Universiteit, 2014.
Zhao, et al. "The study of the feasibility of segmental bone defect repair with tissue-engineered bone membrane: a qualitative observation," Strat. Traum, Limb Recon. (2008) 3:57-64.
Lin et al.,"Commonly used mesenchymal stem cell markers and tracking labels: Limitations and challenges," Histol. Histopathol. 28:1109-1116 (2013).
Medtronic Product Brochure: Infuse Bone Graft, retrieved from the internet Mar. 5, 2017: (www.infusebonegraft.com/healthcare-providers/bone-grafting-options/categorization-of-bone-grafts/allograft-tissue/index.htm).
Sakaguchi et al., Comparison of human stem cells derived from various mesenchymal tissues, Arthritis & Rheumatism, vol. 52, No. 8, Aug. 2005, pp. 2521-2529.
Simper, et al., "Smooth Muscle Progenitor Cells in Human Blood", Circulation (by the American Heart Association), vol. 106, pp. 1199-1204, Aug. 19, 2002.

* cited by examiner

ALLOGRAFTS COMBINED WITH TISSUE DERIVED STEM CELLS FOR BONE HEALING

CROSS-REFERENCES TO RELATED APPLICATIONS

This application is a continuation of U.S. application Ser. No. 12/612,583, filed Nov. 4, 2009, which claims the benefit under 35 U.S.C. §119 (e) of U.S. Provisional Patent Application No. 61/116,484, filed Nov. 20, 2008, both of which are hereby incorporated herein by reference in their entireties.

BACKGROUND OF THE INVENTION

Regenerative medicine requires an abundant source of human adult stem cells that can be readily available at the point of care.

Adipose-derived stem cells (ASCs), which can be obtained in large quantities, have been utilized as cellular therapy for the induction of bone formation in tissue engineering strategies.

Allografts may be combined with stem cells. This requires a significant amount of tissue processing and cellular processing prior to seeding the allograft substrate.

Allografts seeded with living cells generally provide better surgical results.

BRIEF SUMMARY OF THE INVENTION

In an embodiment, there is provided a method of combining mesenchymal stem cells with a bone substrate, the method comprising obtaining adipose tissue having the mesenchymal stem cells together with unwanted cells; digesting the adipose tissue to form a cell suspension having the mesenchymal stem cells and the unwanted cells; adding the cell suspension with the mesenchymal stem cells to seed the bone substrate so as to form a seeded bone substrate; culturing the mesenchymal stem cells on the seeded bone substrate for a period of time to allow the mesenchymal stem cells to adhere to the bone substrate; and rinsing the bone substrate to remove the unwanted cells from the bone substrate.

In another embodiment, there is provided an allograft product including a combination of mesenchymal stem cells with a bone substrate, and the combination manufactured by obtaining adipose tissue having the mesenchymal stem cells together with unwanted cells; digesting the adipose tissue to form a cell suspension having the mesenchymal stem cells and the unwanted cells; adding the cell suspension with the mesenchymal stem cells to seed the bone substrate so as to form a seeded bone substrate; culturing the mesenchymal stem cells on the seeded bone substrate for a period of time to allow the mesenchymal stem cells to adhere to the bone substrate; and rinsing the bone substrate to remove the unwanted cells from the bone substrate.

In still another embodiment, there is provided a method of combining mesenchymal stem cells with a bone substrate, the method comprising obtaining adipose tissue having the mesenchymal stem cells together with unwanted cells; digesting the adipose tissue to form a cell suspension having the mesenchymal stem cells and the unwanted cells to acquire a stromal vascular fraction, and the digesting includes making a collagenase I solution, and filtering the solution through a 0.2 µm filter unit, mixing the adipose solution with the collagenase I solution, and adding the adipose solution mixed with the collagenase I solution to a shaker flask; placing the shaker with continuous agitation at about 75 RPM for about 45 to 60 minutes so as to provide the adipose tissue with a visually smooth appearance; aspirating a supernatant containing mature adipocytes so as to provide a pellet; adding the cell suspension with the mesenchymal stem cells to seed the bone substrate so as to form a seeded bone substrate; culturing the mesenchymal stem cells on the seeded bone substrate for a period of time to allow the mesenchymal stem cells to adhere to the bone substrate; and rinsing the bone substrate to remove the unwanted cells from the bone substrate.

In yet another embodiment, there is provided an allograft product including a combination of mesenchymal stem cells with a bone substrate, and the combination manufactured by obtaining adipose tissue having the mesenchymal stem cells together with unwanted cells; digesting the adipose tissue to form a cell suspension having the mesenchymal stem cells and the unwanted cells to acquire a stromal vascular fraction, and the digesting includes making a collagenase I solution, and filtering the solution through a 0.2 µm filter unit, mixing the adipose solution with the collagenase I solution, and adding the adipose solution mixed with the collagenase I solution to a shaker flask; placing the shaker with continuous agitation at about 75 RPM for about 45 to 60 minutes so as to provide the adipose tissue with a visually smooth appearance; aspirating a supernatant containing mature adipocytes so as to provide a pellet; adding the cell suspension with the mesenchymal stem cells to seed the bone substrate by adding the pellet onto the bone substrate so as to form a seeded bone substrate; culturing the mesenchymal stem cells on the seeded bone substrate for a period of time to allow the mesenchymal stem cells to adhere to the bone substrate; and rinsing the bone substrate to remove the unwanted cells from the bone substrate.

In an embodiment, there is provided a method of combining mesenchymal stem cells with a bone substrate, the method comprising obtaining tissue having the mesenchymal stem cells together with unwanted cells; digesting the tissue to form a cell suspension having the mesenchymal stem cells and the unwanted cells; adding the cell suspension with the mesenchymal stem cells to seed the bone substrate so as to form a seeded bone substrate; culturing the mesenchymal stem cells on the seeded bone substrate for a period of time to allow the mesenchymal stem cells to adhere to the bone substrate; and rinsing the bone substrate to remove the unwanted cells from the bone substrate.

In another embodiment, there is provided an allograft product including a combination of mesenchymal stem cells with a bone substrate, and the combination manufactured by obtaining tissue having the mesenchymal stem cells together with unwanted cells; digesting the tissue to form a cell suspension having the mesenchymal stem cells and the unwanted cells; adding the cell suspension with the mesenchymal stem cells to seed the bone substrate so as to form a seeded bone substrate; culturing the mesenchymal stem cells on the seeded bone substrate for a period of time to allow the mesenchymal stem cells to adhere to the bone substrate; and rinsing the bone substrate to remove the unwanted cells from the bone substrate.

In still another embodiment, there is provided a method of combining mesenchymal stem cells with a bone substrate, the method comprising obtaining bone marrow tissue having the mesenchymal stem cells together with unwanted cells; digesting the bone marrow tissue to form a cell suspension having the mesenchymal stem cells and the unwanted cells; adding the cell suspension with the mesenchymal stem cells to seed the bone substrate so as to form a seeded bone substrate; culturing the mesenchymal stem cells on the seeded bone substrate for a period of time to allow the mesenchymal stem cells to adhere to the bone substrate; and rinsing the bone substrate to remove the unwanted cells from the bone substrate.

In yet another embodiment, there is provided an allograft product including a combination of mesenchymal stem cells with a bone substrate, and the combination manufactured by obtaining bone marrow tissue having the mesenchymal stem cells together with unwanted cells; digesting the bone marrow tissue to form a cell suspension having the mesenchymal stem cells and the unwanted cells; adding the cell suspension with the mesenchymal stem cells to seed the bone substrate so as to form a seeded bone substrate; culturing the mesenchymal stem cells and the bone substrate for a period of time to allow the mesenchymal stem cells to adhere to the bone substrate; and rinsing the bone substrate to remove the unwanted cells from the bone substrate.

In an embodiment, there is provided a method of combining mesenchymal stem cells with a bone substrate, the method comprising obtaining muscle tissue having the mesenchymal stem cells together with unwanted cells; digesting the muscle tissue to form a cell suspension having the mesenchymal stem cells the unwanted cells; adding the cell suspension with the mesenchymal stem cells to seed the bone substrate so as to form a seeded bone substrate; culturing the mesenchymal stem cells on the seeded bone substrate for a period of time to allow the mesenchymal stem cells to adhere to the bone substrate; and rinsing the bone substrate to remove the unwanted cells from the bone substrate.

In another embodiment, there is provided an allograft product including a combination of mesenchymal stem cells with a bone substrate, and the combination manufactured by obtaining muscle tissue having the mesenchymal stem cells together with unwanted cells; digesting the muscle tissue to form a cell suspension having the mesenchymal stem cells and the unwanted cells; adding the cell suspension with the mesenchymal stem cells to seed the bone substrate so as to form a seeded bone substrate; culturing the mesenchymal stem cells on the seeded bone substrate for a period of time to allow the mesenchymal stem cells to adhere to the bone substrate; and rinsing the bone substrate to remove the unwanted cells from the bone substrate.

Other embodiments are also disclosed.

BRIEF DESCRIPTION OF THE DRAWINGS

Illustrative embodiments of the invention are illustrated in the drawings, in which:

FIGS. 3A-3D illustrate various examples of strips (FIG. 3A and FIG. 3D) and dowels (FIG. 3C and FIG. 3D) which have a 3-D cancellous matrix structure and mesenchymal stem cells (MSCs) may adhere to;

DETAILED DESCRIPTION OF THE INVENTION

Figure 1:
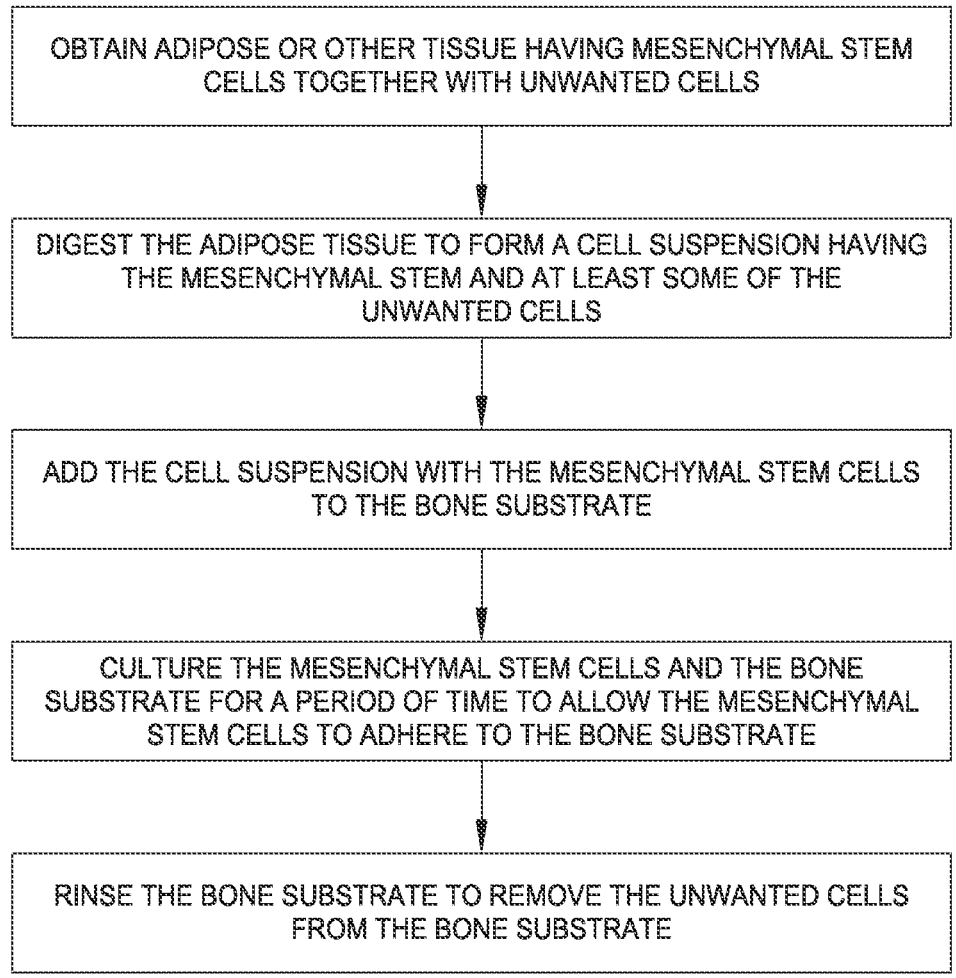
FIG. 1 illustrates a flow chart of the combination of mesenchymal stem cells with a bone substrate.

Unless otherwise described, human adult stem cells are generally referred to as mesenchymal stem cells or MSCs. MSCs are pluripotent cells that have the capacity to differentiate in accordance with at least two discrete development pathways. Adipose-derived stem cells or ASCs are stem cells that are derived from adipose tissue. Stromal Vascular Fraction or SVF generally refers to the centrifuged cell pellet obtained after digestion of tissue containing MScs. In one embodiment, the pellet may include multiple types of stem cells. These stem cells may include, for example, one or more of hematopoietic stem cells, epithelial progenitor cells, and mesenchymal stem cells. In an embodiment, mesenchymal stem cells are filtered from other stem cells by their adherence to a bone substrate, while the other stem cells (i.e., unwanted cells) do not adhere to the bone substrate. Other cells that do not adhere to the bone substrate may also be included in these unwanted cells.

Adipose derived stem cells may be isolated from cadavers and characterized using flow cytometry and tri-lineage differentiation (osteogenesis, chondrogenesis and adipogenesis) may be performed in vitro. The final product may be characterized using histology for microstructure and biochemical assays for cell count. This consistent cell-based product may be useful for bone regeneration.

Tissue engineering and regenerative medicine approaches offer great promise to regenerate bodily tissues. The most widely studied tissue engineering approaches, which are based on seeding and in vitro culturing of cells within the scaffold before implantation, is the cell source and the ability to control cell proliferation and differentiation. Many researchers have demonstrated that adipose tissue-derived stem cells (ASCs) possess multiple differentiation capacities. See, for example, the following, which are incorporated by reference:

Rada, T., R. L. Reis, and M. E. Gomes, *Adipose Tissue-Derived Stem Cells and Their Application in Bone and Cartilage Tissue Engineering.* Tissue Eng Part B Rev, 2009.

Ahn, H. H., et al., *In vivo osteogenic differentiation of human adipose-derived stem cells in an injectable in situ forming gel scaffold.* Tissue Eng Part A, 2009. 15(7): p. 1821-32.

Anghileri, E., et al., *Neuronal differentiation potential of human adipose-derived mesenchymal stem cells.* Stem Cells Dev, 2008. 17(5): p. 909-16.

Arnalich-Montiel, F., et al., *Adipose-derived stem cells are a source for cell therapy of the corneal stroma.* Stem Cells, 2008. 26(2): p. 570-9.

Bunnell, B. A., et al., *Adipose-derived stem cells: isolation, expansion and differentiation.* Methods, 2008. 45(2): p. 115-20.

Chen, R. B., et al., *[Differentiation of rat adipose-derived stem cells into smooth-muscle-like cells in vitro].* Zhonghua Nan Ke Xue, 2009. 15(5): p. 425-30.

Cheng, N. C., et al., *Chondrogenic differentiation of adipose-derived adult stem cells by a porous scaffold derived from native articular cartilage extracellular matrix.* Tissue Eng Part A, 2009. 15(2): p. 231-41.

Cui, L., et al., *Repair of cranial bone defects with adipose derived stem cells and coral scaffold in a canine model.* Biomaterials, 2007. 28(36): p. 5477-86.

de Girolamo, L., et al., *Osteogenic differentiation of human adipose-derived stem cells: comparison of two different inductive media*. J Tissue Eng Regen Med, 2007. 1(2): p. 154-7.

Elabd, C., et al., *Human adipose tissue-derived multipotent stem cells differentiate in vitro and in vivo into osteocyte-like cells*. Biochem Biophys Res Commun, 2007. 361(2): p. 342-8.

Flynn, L., et al., *Adipose tissue engineering with naturally derived scaffolds and adipose-derived stem cells*. Biomaterials, 2007. 28(26): p. 3834-42.

Flynn, L. E., et al., *Proliferation and differentiation of adipose-derived stem cells on naturally derived scaffolds*. Biomaterials, 2008. 29(12): p. 1862-71.

Fraser, J. K., et al., *Adipose-derived stem cells*. Methods Mol Biol, 2008. 449: p. 59-67.

Gimble, J. and F. Guilak, *Adipose-derived adult stem cells: isolation, characterization, and differentiation potential*. Cytotherapy, 2003. 5(5): p. 362-9.

Gimble, J. M. and F. Guilak, *Differentiation potential of adipose derived adult stem (ADAS) cells*. Curr Top Dev Biol, 2003. 58: p. 137-60.

Jin, X. B., et al., *Tissue engineered cartilage from hTGF beta2 transduced human adipose derived stem cells seeded in PLGA/alginate compound in vitro and in vivo*. J Biomed Mater Res A, 2008. 86(4): p. 1077-87.

Kakudo, N., et al., *Bone tissue engineering using human adipose-derived stem cells and honeycomb collagen scaffold*. J Biomed Mater Res A, 2008. 84(1): p. 191-7.

Kim, H. J. and G. I. Im, *Chondrogenic differentiation of adipose tissue-derived mesenchymal stem cells: greater doses of growth factor are necessary*. J Orthop Res, 2009. 27(5): p. 612-9.

Kingham, P. J., et al., *Adipose-derived stem cells differentiate into a Schwann cell phenotype and promote neurite outgrowth in vitro*. Exp Neural, 2007. 207(2): p. 267-74.

Mehlhorn, A. T., et al., *Chondrogenesis of adipose-derived adult stem cells in a poly-lactide-co-glycolide scaffold*. Tissue Eng Part A, 2009. 15(5): p. 1159-67.

Merceron, C., et al., *Adipose-derived mesenchymal stem cells and biomaterials for cartilage tissue engineering*. Joint Bone Spine, 2008. 75(6): p. 672-4.

Mischen, B. T., et al., *Metabolic and functional characterization of human adipose-derived stem cells in tissue engineering*. Plast Reconstr Surg, 2008. 122(3): p. 725-38.

Mizuno, H., *Adipose-derived stem cells for tissue repair and regeneration: ten years of research and a literature review*. J Nippon Med Sch, 2009. 76(2): p. 56-66.

Tapp, H., et al., *Adipose-Derived Stem Cells: Characterization and Current Application in Orthopaedic Tissue Repair*. Exp Biol Med (Maywood), 2008.

Tapp, H., et al., *Adipose-derived stem cells: characterization and current application in orthopaedic tissue repair*. Exp Biol Med (Maywood), 2009. 234(1): p. 1-9.

van Dijk, A., et al., *Differentiation of human adipose-derived stem cells towards cardiomyocytes is facilitated by laminin*. Cell Tissue Res, 2008. 334(3): p. 457-67.

Wei, Y., et al., *A novel injectable scaffold for cartilage tissue engineering using adipose-derived adult stem cells*. J Orthop Res, 2008. 26(1): p. 27-33.

Wei, Y., et al., *Adipose-derived stem cells and chondrogenesis*. Cytotherapy, 2007. 9(8): p. 712-6.

Zhang, Y. S., et al., *[Adipose tissue engineering with human adipose-derived stem cells and fibrin glue injectable scaffold]*. Zhonghua Yi Xue Za Zhi, 2008. 88(38): p. 2705-9.

Additionally, adipose tissue is probably the most abundant and accessible source of adult stem cells. Adipose tissue derived stem cells have great potential for tissue regeneration. Nevertheless, ASCs and bone marrow-derived stem cells (BMSCs) are remarkably similar with respect to growth and morphology, displaying fibroblastic characteristics, with abundant endoplasmic reticulum and large nucleus relative to the cytoplasmic volume. See, for example, the following, which are incorporated by reference:

Gimble, J. and F. Guilak, *Adipose-derived adult stem cells: isolation, characterization, and differentiation potential*. Cytotherapy, 2003. 5(5): p. 362-9.

Gimble, J. M. and F. Guilak, *Differentiation potential of adipose derived adult stem (ADAS) cells*. Curr Top Dev Bioi, 2003. 58: p. 137-60.

Strem, B. M., et al., *Multipotential differentiation of adipose tissue-derived stem cells*. Keio J Med, 2005. 54(3): p. 132-41.

De Ugarte, D. A., et al., *Comparison of multi-lineage cells from human adipose tissue and bone marrow*. Cells Tissues Organs, 2003. 174(3): p. 101-9.

Hayashi, O., et al., *Comparison of osteogenic ability of rat mesenchymal stem cells from bone marrow, periosteum, and adipose tissue*. Calcif Tissue Int. 2008. 82(3): p. 238-47.

Kim, Y., et al., *Direct comparison of human mesenchymal stem cells derived from adipose tissues and bone marrow in mediating neovascularization in response to vascular ischemia*. Cell Physiol Biochem, 2007. 20(6): p. 867-76.

Lin, L., et al., *Comparison of osteogenic potentials of BMP4 transduced stem cells from autologous bone marrow and fat tissue in a rabbit model of calvarial defects*. Calcif Tissue Int, 2009. 85(1): p. 55-65.

Niemeyer, P., et al., *Comparison of immunological properties of bone marrow stromal cells and adipose tissue-derived stem cells before and after osteogenic differentiation in vitro*. Tissue Eng, 2007. 13(1): p. 111-21.

Noel, D., et al., *Cell specific differences between human adipose-derived and mesenchymal-stromal cells despite similar differentiation potentials*. Exp Cell Res, 2008. 314(7): p. 1575-84.

Yoo, K. H., et al., *Comparison of immunomodulatory properties of mesenchymal stem cells derived from adult human tissues*. Cell Immunol, 2009.

Yoshimura, H., et al., *Comparison of rat mesenchymal stem cells derived from bone marrow, synovium, periosteum, adipose tissue, and muscle*. Cell Tissue Res, 2007. 327(3): p. 449-62.

Other common characteristics of ASCs and BMSCs can be found in the transcriptional and cell surface profile. Several studies have already been done in the field of bone tissue engineering using ASCs. See, for example, the following, which are incorporated by reference:

Rada, T., R. L. Reis, and M. E. Gomes, *Adipose Tissue-Derived Stem Cells and Their Application in Bone and Cartilage Tissue Engineering*. Tissue Eng Part B Rev, 2009.

Tapp, H., et al., *Adipose-Derived Stem Cells: Characterization and Current Application in Orthopaedic Tissue Repair*. Exp Bioi Med (Maywood), 2008.

Tapp, H., et al., *Adipose-derived stem cells: characterization and current application in orthopaedic tissue repair*. Exp Bioi Med (Maywood), 2009. 234(1): p. 1-9.

De Girolamo, L., et al., *Human adipose-derived stem cells as future tools in tissue regeneration: osteogenic differentiation and cell-scaffold interaction*. Int J Artif Organs, 2008. 31(6): p. 467-79.

Di Bella, C., P. Farlie, and A. J. Penington, *Bone regeneration in a rabbit critical-sized skull defect using autologous adipose-derived cells*. Tissue Eng Part A, 2008. 14(4): p. 483-90.

Grewal, N. S., et al., *BMP-2 does not influence the osteogenic fate of human adipose-derived stem cells*. Plast Reconstr Surg, 2009. 123(2 Suppl): p. 158S-65S.

Li, H., et al., *Bone regeneration by implantation of adipose-derived stromal cells expressing BMP-2*. Biochem Biophys Res Commun, 2007. 356(4): p. 836-42.

Yoon, E., et al., *In vivo osteogenic potential of human adipose-derived stem cells/poly lactide-co-glycolic acid constructs for bone regeneration in a rat critical-sized calvarial defect model*. Tissue Eng, 2007. 13(3): p. 619-27.

These studies have demonstrated that stem cells obtained from the adipose tissue exhibit good attachment properties to most of the material surfaces and the capacity to differentiate into osteoblastic-like cells in vitro and in vivo. Recently it has been shown that ASCs may stimulate the vascularization process. See, for example, the following, which are incorporated by reference:

Butt, O. I., et al., *Stimulation of peri-implant vascularization with bone marrow-derived progenitor cells: monitoring by in vivo EPRoximetry*. TissueEng, 2007. 13(8): p. 2053-61.

Rigotti, G., et al., *Clinical treatment of radiotherapy tissue damage by lipoaspirate transplant: a healing process mediated by adipose-derived adult stem cells*. Plast Reconstr Surg, 2007. 119(5): p. 1409-22; discussion 1423-4.

Demineralized bone substrate, as an allogeneic material, is a promising bone tissue-engineering scaffold due to its close relation to autologous bone in terms of structure and function. Combined with MSCs, these scaffolds have been demonstrated to accelerate and enhance bone formation within osseous defects when compared with the matrix alone. See, for example, the following, which are incorporated by reference:

Chen, L. Q., et al., *[Study of MSCs in vitro cultured on demineralized bone matrix of mongrel]*. Shanghai Kou Qiang Yi Xue, 2007. 16(3): p. 255-8.

Gamradt, S. C. and J. R. Lieberman, *Bone graft for revision hip arthroplasty: biology and future applications*. Clin Orthop Relat Res, 2003(417): p. 183-94.

Honsawek, S., D. Dhitiseith, and V. Phupong, *Effects of demineralized bone matrix on proliferation and osteogenic differentiation of mesenchymal stem cells from human umbilical cord*. J Med Assoc Thai, 2006. 89 Suppl 3: p. S189-95.

Kasten, P., et al., *[Induction of bone tissue on different matrices: an in vitro and a in vivo pilot study in the SCID mouse]*. Z Orthop Ihre Grenzgeb, 2004.142(4): p. 467-75.

Kasten, P., et al., *Ectopic bone formation associated with mesenchymal stem cells in a resorbable calcium deficient hydroxyapatite carrier*. Biomaterials, 2005. 26(29): p. 5879-89.

Qian, Y., Z. Shen, and Z. Zhang, *[Reconstruction of bone using tissue engineering and nanoscale technology]*. Zhongguo Xiu Fu Chong Jian Wai Ke Za Zhi, 2006. 20(5): p. 560-4.

Reddi, A. H., *Role of morphogenetic proteins in skeletal tissue engineering and regeneration*. Nat Biotechnol, 1998. 16(3): p. 247-52.

Reddi, A. H., *Morphogenesis and tissue engineering of bone and cartilage: inductive signals, stem cells, and biomimetic biomaterials*. Tissue Eng, 2000.6(4): p. 351-9.

Tsiridis, E., et al., *In vitro and in vivo optimization of impaction allografting by demineralization and addition of rh-OP*-1. J Orthop Res, 2007. 25(11): p. 1425-37.

Xie, H., et al., *The performance of a bone-derived scaffold material in the repair of critical bone defects in a rhesus monkey model*. Biomaterials, 2007.28(22): p. 3314-24.

Liu, G., et al., *Tissue-engineered bone formation with cryopreserved human bone marrow mesenchymal stem cells*. Cryobiology, 2008. 56(3): p. 209-15.

Liu, G., et al., *Evaluation of partially demineralized osteoporotic cancellous bone matrix combined with human bone marrow stromal cells for tissue engineering: an in vitro and in vivo study*. Calcif Tissue Int, 2008. 83(3): p. 176-85.

Liu, G., et al., *Evaluation of the viability and osteogenic differentiation of cryopreserved human adipose-derived stem cells*. Cryobiology, 2008. 57(1): p. 18-24.

As discussed herein, human ASCs seeded bone substrates may be characterized in terms of microstructure, cell number and cell identity using histology, biochemical assay and flow cytometry. In an embodiment, these substrates may include bone material which has been previously subjected to a demineralization process.

Figure 2:
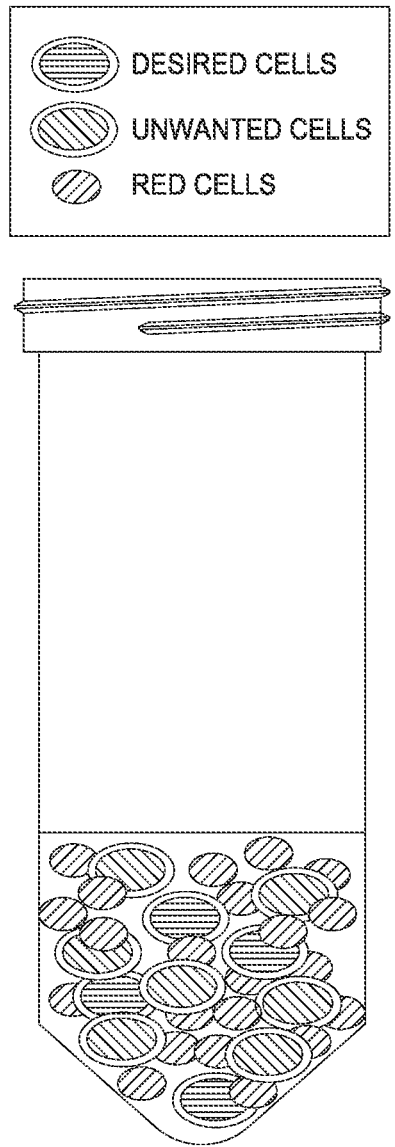
FIG. 2 illustrates a prior art example of a pellet of a stromal vascular fraction containing the desired stem cells and unwanted cells.

FIG. 1 is a flow chart of a process for making an allograft with stem cells product. In an embodiment, a stromal vascular fraction may be used to seed the allograft. It should be apparent from the present disclosure that the term "seed" relates to addition and placement of the stem cells within, or at least in attachment to, the allograft, but is not limited to a specific process. FIG. 2 illustrates a pellet of the stromal vascular fraction containing the desired stem cells.

In an exemplary embodiment, a method of combining mesenchymal stem cells with a bone substrate is provided. The method may include obtaining adipose tissue having the mesenchymal stem cells together with unwanted cells. Unwanted cells may include hematopoietic stem cells and other stromal cells. The method may further include digesting the adipose tissue to form a cell suspension having the mesenchymal stem cells and at least some or all of the unwanted cells. In another embodiment, this may be followed by negatively depleting some of the unwanted cells and other constituents to concentrate mesenchymal stem cells.

Next, the method includes adding the cell suspension with the mesenchymal stem cells to the bone substrate. This may be followed by culturing the mesenchymal stem cells and the bone substrate for a period of time to allow the mesenchymal stem cells to adhere to the bone substrate. In order to provide a desired product, the method includes rinsing the bone substrate to remove the unwanted cells from the bone substrate.

In one embodiment, an allograft product may include a combination of mesenchymal stem cells with a bone substrate such that the combination is manufactured by the above exemplary embodiment.

In an embodiment, the adipose tissue may be obtained from a cadaveric donor. A typical donor yields 2 liters of adipose containing 18 million MSCs. In one embodiment, a bone substrate may be from the same cadaveric donor as the adipose tissue. In another embodiment, the adipose tissue may be obtained from a patient. In addition, both the bone substrate and the adipose tissue may be obtained from the same patient. This may include, but is not limited to, removal of a portion of the ilium (e.g., the iliac crest) may be removed from the patient by a surgical procedure and adipose cells may be removed using liposuction. Other sources, and combination of sources, of adipose tissue, other tissues, and bone substrates may be utilized.

Optionally, the adipose tissue may be washed prior to or during digestion. Washing may include using a thermal shaker at 75 RPM at 37° C. for at least 10 minutes. Washing the adipose tissue may include washing with a volume of PBS substantially equal to the adipose tissue. In an embodiment, washing the adipose tissue includes washing with the PBS with 1% penicillin and streptomycin at about 37° C.

For example, washing the adipose tissue may include agitating the tissue and allowing phase separation for about 3 to 5 minutes. This may be followed by aspirating off an infranatant solution. The washing may include repeating washing the adipose tissue multiple times until a clear infranatant solution is obtained. In one embodiment, washing the adipose tissue may include washing with a volume of growth media substantially equal to the adipose tissue.

In another exemplary embodiment, a method of combining mesenchymal stem cells with a bone substrate is provided. The method may include obtaining bone marrow tissue having the mesenchymal stem cells together with unwanted cells. Unwanted cells may include hematopoietic stem cells and other stromal cells. The method may further include digesting the bone marrow tissue to form a cell suspension having the mesenchymal stem cells and the unwanted cells. In another embodiment, this may be followed by naturally selecting MSCs and depleting some of the unwanted cells and other constituents to concentrate mesenchymal stem cells.

Next, the method includes adding the cell suspension with the mesenchymal stem cells to the bone substrate. This may be followed by culturing the mesenchymal stem cells and the bone substrate for a period of time to allow the mesenchymal stem cells to adhere to the bone substrate. In order to provide a desired product, the method includes rinsing the bone substrate to remove the unwanted cells from the bone substrate.

In one embodiment, an allograft product may include a combination of mesenchymal stem cells with a bone substrate such that the combination is manufactured by the above exemplary embodiment.

In another exemplary embodiment, a method of combining mesenchymal stem cells with a bone substrate is provided. The method may include obtaining muscle tissue having the mesenchymal stem cells together with unwanted cells. Unwanted cells may include hematopoietic stem cells and other stromal cells. The method may further include digesting the muscle tissue to form a cell suspension having the mesenchymal stem cells and the unwanted cells. In another embodiment, this may be followed by naturally selecting MSCs to concentrate mesenchymal stem cells.

Next, the method includes adding the cell suspension with the mesenchymal stem cells to the bone substrate. This may be followed by culturing the mesenchymal stem cells and the bone substrate for a period of time to allow the mesenchymal stem cells to adhere to the bone substrate. In order to provide a desired product, the method includes rinsing the bone substrate to remove the unwanted cells from the bone substrate.

In one embodiment, an allograft product may include combination of mesenchymal stem cells with a bone substrate such that the combination is manufactured by the above exemplary embodiment.

In another exemplary embodiment, a method of combining mesenchymal stem cells with a bone substrate is provided. The method may include obtaining tissue having the mesenchymal stem cells together with unwanted cells. Unwanted cells may include hematopoietic stem cells and other stromal cells.

The method may further include digesting the tissue to form a cell suspension having the mesenchymal stem cells and at least some of the unwanted cells. In another embodiment, this may be followed by negatively depleting some of the unwanted cells and other constituents to concentrate mesenchymal stem cells.

Next, the method includes adding the cell suspension with the mesenchymal stem cells to the bone substrate. In an embodiment, this substrate may include a bone material which has been subjected to a demineralization process. In another embodiment, this substrate may be a non-bone material, which may include (but is not limited to) a collagen based material. This may be followed by culturing the mesenchymal stem cells and the bone substrate for a period of time to allow the mesenchymal stem cells to adhere to the bone substrate. In order to provide a desired product, the method includes rinsing the bone substrate to remove the unwanted cells from the bone substrate.

In one embodiment, an allograft product may include a combination of mesenchymal stem cells with a bone substrate such that the combination is manufactured by the above exemplary embodiment.

Digesting the cell suspension may include making a collagenase I solution, and filtering the solution through a 0.2 μm filter unit, mixing the adipose tissue with the collagenase I solution, and adding the cell suspension mixed with the collagenase I solution to a shaker flask. Digesting the cell suspension may further include placing the shaker with continuous agitation at about 75 RPM for about 45 to 60 minutes so as to provide the adipose tissue with a visually smooth appearance.

Digesting the cell suspension may further include aspirating supernatant containing mature adipocytes so as to provide a pellet, which may be referred to as a stromal vascular fraction. (See, for example, FIG. 2.) Prior to seeding, a lab sponge or other mechanism may be used to pat dry bone substrate.

In one embodiment, adding the cell suspension with the mesenchymal stem cells to the bone substrate may include using a cell pellet for seeding onto the bone substrate. In an embodiment, adding the cell suspension with the mesenchymal stem cells to the bone substrate may include using a cell pellet for seeding onto the bone substrate. In another embodiment, adding the cell suspension with the mesenchymal stem cells to the bone substrate may include using a cell pellet for seeding onto the bone substrate of cortical bone. In another embodiment, adding the cell suspension with the mesenchymal stem cells to the bone substrate may include adding the cell pellet onto the bone substrate of cancellous bone. In another embodiment, adding the cell suspension with the mesenchymal stem cells to the bone substrate may include adding the cell pellet onto the bone substrate of ground bone. In another embodiment, adding the cell suspension with the mesenchymal stem cells to the bone substrate may include adding the cell pellet onto the bone substrate of cortical/cancellous bone. In another embodiment, adding the cell suspension with the mesenchymal stem cells to the bone substrate may include adding the cell pellet onto the bone substrate of demineralized cancellous bone.

In an embodiment, the method may include placing the bone substrate into a cryopreservation media after rinsing the bone substrate. This cryopreservation media may be provided to store the final products. For example, the method may include maintaining the bone substrate into a frozen state after rinsing the bone substrate to store the final products. The frozen state may be at about negative 80° C.

In another embodiment, Ficoll density solution may be utilized. For example, negatively depleting the concentration of the mesenchymal stem cells may include adding a volume of PBS and a volume of Ficoll density solution to the adipose solution. The volume of PBS may be 5 ml and the volume of Ficoll density solution may be 25 ml with a density of 1.073 g/ml. Negatively depleting the concentration of the mesenchymal stem cells may also include centrifuging the adipose solution at about 1160 g for about 30 minutes at about room temperature. In one embodiment, the method may include stopping the centrifuging the adipose solution without using a brake.

Negatively depleting the concentration of the mesenchymal stem cells is optional and may next include collecting an upper layer and an interface containing nucleated cells, and discarding a lower layer of red cells and cell debris. Negatively depleting the concentration of the mesenchymal stem cells may also include adding a volume of D-PBS of about twice an amount of the upper layer of nucleated cells, and inverting a container containing the cells to wash the collected cells. Negatively depleting the concentration of the mesenchymal stem cells may include centrifuging the collected cells to pellet the collected cells using the break during deceleration.

In an embodiment, negatively depleting the concentration of the mesenchymal stem cells may further include centrifuging the collected cells at about 900 g for about 5 minutes at about room temperature. Negatively depleting some of the unwanted cells may include discarding a supernatant after centrifuging the collected cells, and resuspending the collected cells in a growth medium.

In one embodiment, adding the cell suspension with the mesenchymal stem cells to the bone substrate may include adding the cell pellet onto the bone substrate. Adding the solution with the mesenchymal stem cells to the bone substrate may include adding cell pellet onto the bone substrate which was subjected to a demineralization process. In another embodiment, adding the cell suspension with the mesenchymal stem cells to the bone substrate may include adding the cell pellet onto the bone substrate of cortical bone. In an embodiment, adding the cell suspension with the mesenchymal stem cells to the bone substrate includes adding the cell pellet onto the bone substrate of cancellous bone. In another embodiment, adding the cell suspension with the mesenchymal stem cells to the bone substrate may include adding the cell pellet onto the bone substrate of ground bone. In another embodiment, adding the cell suspension with the mesenchymal stem cells to the bone substrate may include adding the cell pellet onto the bone substrate of cortical/cancellous bone. In another embodiment, adding the cell suspension with the mesenchymal stem cells to the bone substrate may include adding the cell pellet onto the bone substrate of demineralized cancellous bone.

In an embodiment, the method may further include placing the bone substrate into a cryopreservation media after rinsing the bone substrate. This cryopreservation media may be provided to store the final products. The method may include maintaining the bone substrate into a frozen state after rinsing the bone substrate to store the final products. The frozen state may be at about negative 80° C.

The seeded allografts are cultured for a period of time to allow the mesenchymal stem cells to adhere to the bone substrate. The unwanted cells were rinsed and removed from the bone substrate. After culturing, a lab sponge or other mechanism may be used to pat dry the bone substrate.

The mesenchymal stem cells are anchorage dependent. The mesenchymal stem cells naturally adhere to the bone substrate. The mesenchymal stem cells are non-immunogenic and regenerate bone. The unwanted cells are generally anchorage independent. This means that the unwanted cells generally do not adhere to the bone substrate. The unwanted cells may be immunogenic and may create blood and immune system cells. For cell purification during a rinse, mesenchymal stem cells adhere to the bone while unwanted cells, such as hematopoietic stem cells, are rinsed away leaving a substantially uniform population of mesenchymal stem cells on the bone substrate.

The ability to mineralize the extracellular matrix and to generate bone is not unique to MSCs. In fact, ASCs possess a similar ability to differentiate into osteoblasts under similar conditions. Human ASCs offer a unique advantage in contrast to other cell sources. The multipotent characteristics of ASCs, as wells as their abundance in the human body, make these cells a desirable source in tissue engineering applications.

Figure 3A:
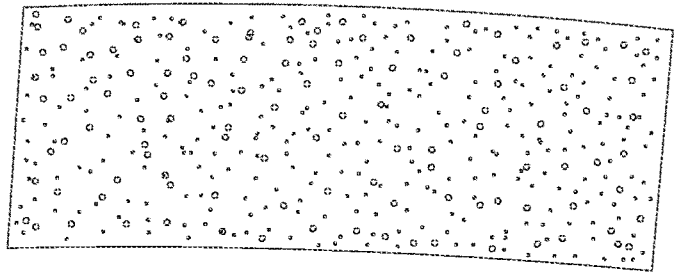
Figure 3B:
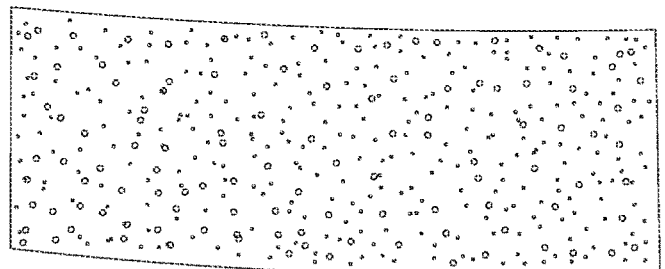
Figure 3C:
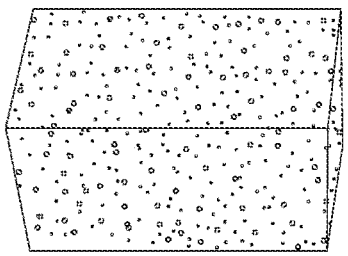
Figure 3D:
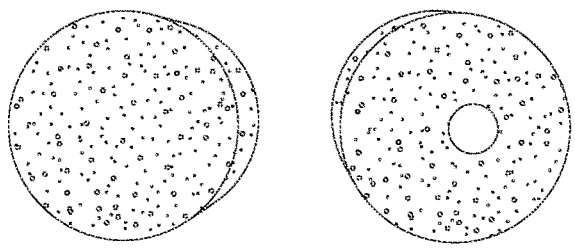

In various embodiments, bone substrates (e.g., cortical cancellous dowels, strips, cubes, blocks, discs, and granules, as well as other substrates formed in dowels, strips, cubes, blocks, discs, and granules) may be subjected to a demineralization process to remove blood, lipids and other cells so as to leave a matrix. FIGS. 3A-3D illustrate various examples of strips (FIGS. 3A and 3B) and dowels (FIGS. 3C and 3D). Generally, these substrates may have a 3-D cancellous matrix structure, which MSCs may adhere to.

In addition, this method and combination product involve processing that does not alter the relevant biological characteristics of the tissue. Processing of the adipose/stem cells may involve the use of antibiotics, cell media, collagenase. None of these affects the relevant biological characteristics of the stem cells. The relevant biological characteristics of these mesenchymal stem cells are centered on renewal and repair. The processing of the stem cells does not alter the cell's ability to continue to differentiate and repair.

In the absence of stimulation or environmental cues, mesenchymal stem cells (MSCs) remain undifferentiated and maintain their potential to form tissue such as bone, cartilage, fat, and muscle. Upon attachment to an osteoconductive matrix, MSCs have been shown to differentiate along the osteoblastic lineage in vivo. See, for example, the following, which are incorporated by reference:

Arinzeh T L, Peter S J, Archambault M P, van den Bas C, Gordon S, Kraus K, Smith A, Kadiyala S. *Allogeneic mesenchymal stem cells regenerate bone in a critical sized canine segmental defect*. J Bone Joint Surg Am. 2003; 85-A:1927-35.

Bruder S P, Kurth A A, Shea M, Hayes W C, Jaiswal N, Kadiyala S. *Bone regeneration by implantation of purified, culture-expanded human mesenchymal stem cells*, J Orthop Res. 1998; 16:155-62.

Example 1

Adipose Recovery

Adipose was recovered from cadaveric donors. Adipose aspirate may be collected using liposuction machine and shipped on wet ice.

Washing

Adipose tissue was warmed up in a thermal shaker at RPM=75, 37° C. for 10 min. Adipose was washed with equal volume of pre-warmed phosphate buffered saline (PBS) at 37° C., 1% penicillin/streptomycin. Next, the adipose was agitated to wash the tissue. Phase separation was allowed for about 3 to 5 minutes. The infranatant solution was aspirated. The wash was repeated 3 to 4 times until a clear infranatant solution was obtained.

The solution was suspended in an equal volume of growth media (DMEM/F12, 10% FBS, 1% penicillin/streptomycin) and stored in a refrigerator at about 4° C.

Digestion and Combining of Cell Suspension with Allografts

Digestion of the adipose was undertaken to acquire a stromal vascular fraction (SVF) followed by combining the solution onto an allograft.

Digestion involved making collagenase I solution, including 1% fetal bovine serum (FBS) and 0.1% collagenase I. The solution was filtered through a 0.2 urn filter unit. This solution should be used within 1 hour of preparation.

Next, take out the washed adipose and mix with collagenase I solution at 1:1 ratio. Mixture was added to a shaker flask.

The flask was placed in an incubating shaker at 37° C. with continuous agitation (at about RPM=75) for about 45 to 60 minutes until the tissue appeared smooth on visual inspection.

The digestate was transferred to centrifuge tubes and centrifuged for 5 minutes at about 300-500 g at room temperature. The supernatant, containing mature adipocytes, was then aspirated. The pellet was identified as the stromal vascular fraction (SVF).

Growth media was added into every tube (i.e., 40 ml total was added into the 4 tubes) followed by gentle shaking.

All of the cell mixtures were transferred into a 50 ml centrifuge tube. A 200 µl sample was taken, 50 µl is for initial cell count, and the remainder of the 150 µl was used for flow cytometry.

Aliquot cell mixtures were measured into 2 centrifuge tubes (of 10 ml each) and centrifuged at about 300 g for 5 minutes. The supernatant was aspirated.

A cell pellet obtained from one tube was used for seeding onto allografts. The allografts may include cortical/cancellous or both which was subjected to a demineralization process.

Certain volume of growth medium was added into the cell pellets and shaken to break the pellets. A very small volume of cell suspension was added onto allografts. After culturing in $CO_2$ incubator at 37° C. for a few hours, more growth medium (DMEM/F12, 10% FBS with antibiotics) was added. This was astatic "seeding" process. A dynamic "seeding" process can be used for particular bone substrate. 10 ml of a cell suspension and bone substrate were placed in a 50 ml centrifuge tube on an orbital shaker and agitated at 100 to 300 rpm for 6 hours.

After a few days (about 1 to 3 days), the allograft was taken out and rinsed thoroughly in PBS and sonicated to remove unwanted cells. The allograft was put into cryopreservation media (10% DMSO, 90% serum) and kept frozen at −80° C. The frozen allograft combined with the mesenchymal stem cells is a final product.

Example 2

Adipose Recovery

Adipose was recovered from cadaveric donors. Adipose aspirate may be collected using liposuction machine and shipped on wet ice.

Washing

Adipose tissue was processed in a thermal shaker at RPM=75, 37° C. for 10 min. Adipose was washed with equal volume of pre-warmed phosphate buffered saline (PBS) at 37° C., 1% penicillin/streptomycin. Next, the adipose was agitated to wash the tissue. Phase separation was allowed for about 3 to 5 minutes. The supernatant solution was sucked off. The wash was repeated 3 to 4 times until a clear infranatant solution was obtained.

Acquire Ficoll Concentrated Stem Cells and Combine onto Allograft

Ficoll concentrated stem cells were acquired and seeded onto an allograft. 5 ml PBS was placed into the 50 ml tube with cells and 25 ml of 1.073 g/ml Ficoll density solution was added to the bottom of the tube with a pipet.

The tubes were subjected to centrifugation at 1160 g for 30 min at room temperature and stopped with the brake off. The upper layer and interface, approximately 15 to 17 ml containing the nucleated cells were collected with a pipet and transferred to a new 50 ml disposable centrifuge tube. The lower layer contained red cells and cell debris and was discarded.

Next, 2 volumes of 0-PBS were added. The tubes were capped and mix gently by inversion to wash the cells.

The tubes with the diluted cells were then subjected to centrifugation at 900 g for 5 minutes at room temperature to pellet the cells with the brake on during deceleration.

The supernatant was discarded and the washed cells were resuspended in 10 ml of growth medium. 10 ml of growth media was added into the tube and it was shaken gently. A 1 ml sample was taken with 100 µl is for cell count, and the remainder of 900 µl was used for flow cytometry.

The remainder of the cell mixtures were centrifuged at about 300 g for about 5 minutes. The supernatant was aspirated.

A cell pellet was used for "seeding" onto allografts. Allografts may include demineralized bone, cortical/cancellous bone, or both. A very small volume of medium was added into the cell pellet and shaken. 100 µl of cell mixtures were added onto a 15 mm disc within a 24-well culture plate.

After culturing the allograft in a C02 incubator at about 37° C., 1 ml growth medium (DMEM/F12, 10% FBS with antibiotics) was added. This was a static "seeding" process. A dynamic "seeding" process can be used for a particular bone substrate.

After a few days (about 1 to 3 days), the allograft was taken out and rinsed thoroughly in PBS to remove unwanted cells. The allograft was put into cryopreservation media (10% DMSO, 90% serum) and kept frozen at −80° C. The frozen allograft combined with the stem cells is a final product.

Example 3

Bone Marrow Recovery

Adipose was recovered from cadaveric donors. Adipose aspirate may be collected using liposuction machine and shipped on wet ice.

Washing

The bone marrow sample is washed by adding 6 to 8 volumes of Dulbecco's phosphate buffered saline (D-PBS) in a 50 ml disposable centrifuge, inverting gently and subjecting to centrifugation (800 g for 10 min) to pellet cells to the bottom of the tube.

Acquire Stem Cells and Combine onto Allograft

The supernatant is discarded and the cell pellets from all tubes are resuspended in 1-2 ml of growth medium (DMEM, low glucose, with 10% FBS and 1% pen/strap). The cell mixtures are seeded onto allografts. With a few hours of culture in C02 incubator at 37° C., more growth medium is added. A few days later, the allograft is taken out and rinsed thoroughly in PBS and put into cryopreservation media (10% DMSO, 90% serum) and kept frozen.

Example 4

Skeletal Muscle Recovery

Skeletal muscle may be recovered from cadaveric donors.

Washing

Minced skeletal muscle (1-3 mm cube) is digested in a 3 mg/ml collagenase D solution in α-MEM at 37° C. for 3 hours. The solution is filtered with 100 um nylon mesh. The solution is centrifuged at 500 g for 5 min.

Acquire Stem Cells and Combine onto Allograft

The supernatant is discarded and the cell pellets from all tubes are resuspended in 1-2 ml of growth medium (DMEM, low glucose, with 10% FBS and 1% pen/strap). The cell mixtures are seeded onto allografts. With a few hours of culture in C02 incubator at 37° C., more growth medium will be added. A few days later, the allograft is taken out and rinsed thoroughly in PBS and put into cryopreservation media (10% DMSO, 90% serum) and kept frozen.

Example 5

Adipose Recovery

Adipose was recovered from a cadaveric donor within 24 hours of death and shipped in equal volume of DMEM in wet ice.

Washing

Adipose were washed 3 times with PBS and suspended in an equal volume of PBS supplemented with Collagenase Type I prewarmed to 37° C. The tissue was placed in a shaking water bath at 37° C. with continuous agitation for 45 to 60 minutes and centrifuged for 5 minutes at room temperature. The supernatant, containing mature adipocytes, was aspirated. The pellet was identified as the SVF (stromal vascular fraction).

Cortical Cancellous Bone Recovery

Human cortical cancellous bone was recovered from ilium crest from the same donor. The samples were sectioned into strips (20×50×5 mm), and then they were subjected to a demineralization process with HCl for 3 hours, rinsed with PBS until the pH is neutral.

Digestion and Combining of Cell Suspension with Allograft

The adipose-derived stem cells (ASCs) were added onto the grafts and cultured in C02 incubator at 37° C. Then the allografts were rinsed thoroughly in PBS to remove antibiotics and other debris. At the end, the allografts were put into cryopreservation media and kept frozen at −80° C.

Example 6

Adipose-Derived Stem Cell Characterization

Flow Cytometry Analysis

The following antibodies were used for flow cytometry. PE anti-CD73 (clone AD2) Becton Dickinson, PE anti-CD90 (clone F15-42-1) AbD SeroTec, PE anti-CD105 (clone SN6) AbD SeroTec, PE anti-Fibroblasts/Epithelial Cells (clone 07-FIB) AbD SeroTec, FITC anti-CD34 (clone 8G12) Becton Dickinson, FITC Anti-CD45 (clone 2D1) Becton Dickinson, and PE anti-CD271 (clone ME20.4-1.H4) Miltenyi BioTec. The Isotype controls were FITC Mouse IgG1 Kappa (clone MOPC-21) Becton Dickinson, PE Mouse IgG1 Kappa (clone MOPC-21) Becton Dickinson, and PE Mouse IgG2a Kappa (clone G155-178) Becton Dickinson.

A small aliquot of the cells were stained with a propidium iodide/detergent solution and fluorescent nuclei were counted using a hemocytometer on a fluorescent microscope. This total cell count was used to adjust the number of cells per staining tube to no more than $5.0 \times 10^5$ cells. The cells were washed with flow cytometric wash buffer (PBS supplemented with 2% FBS and 0.1% NaN3), stained with the indicated antibodies and washed again before acquisition. Staining was for 15 minutes at room temperature (15-30DC).

At least 20,000 cells were acquired for each sample on a FACScan flow cytometer equipped with a 15-mW, 488-nm, argon-ion laser (BD Immunocytometry Systems, San Jose, Calif.). The cytometer QC and setup included running SpheroTech rainbow (3 μm, 6 peaks) calibration beads (SpheroTech Inc.) to confirm instrument functionality and linearity. Flow cytometric data were collected and analyzed using Cell Quest software (BD Immunocytometry Systems). The small and large cells were identified by forward (FSC) and side-angle light scatter (SSC) characteristics. Autofluorescence was assessed by acquiring cells on the flow cytometer without incubating with fluorochrome labeled antibodies. Surface antigen expression was determined with a variety of directly labeled antibodies according to the supplier's recommendations. Antibodies staining fewer than 20% of the cells relative to the Isotype-matched negative control were considered negative (this is standard-of-practice for immunophenotyping leukocytes for leukemia lymphoma testing). The viability of the small and large cells was determined using the Becton Dickinson Via-Probe (7-AAD).

In Vitro Tri-Lineage Differentiation

Osteogenesis: Confluent cultures of primary ASCs were induced to undergo osteogenesis by replacing the stromal medium with osteogenic induction medium (® osteogenesis differentiation kit STEMPRO® Osteogeneis Differentiation Kit (ThermoFisher Scientific, previously Invitrogen, Cat # A1007201), a kit used for the osteogenic differentiation of mesenchymal stem cells in tissue culture vessels that contains STEMPRO® Osteocyte/Chondrocyte Differentiation Basal Medium (Gibco® Cat. # A10069) and STEMPRO® Osteogenesis Supplement (Gibco® Cat. # A10066-01). Cultures were fed with fresh osteogenic differentiation medium every 3 to 4 days for a period of up to 3 weeks. Cells were then fixed in 10% neutral buffered formalin and rinsed with Dl water. Osteogenic differentiation was determined by staining for calcium phosphate with Alizarin red (Sigma).

Adipogenesis: Confluent cultures of primary ASCs were induced to undergo adipogenesis by replacing the stromal medium with adipogenic induction medium (STEMPRO® Adipogenesis Differentiation Kit (ThermoFisher Scientific, previously Invitrogen, Cat. # A1007001), a kit used for the adipogenic differentiation of mesenchymal stem cells in tissue culture vessels that contains STEMPRO® Adipocyte Differentiation Basal Medium (Gibco® Cat. # A10410) and STEMPRO® Adipogenesis Supplement (Gibco® Cat. # A10065-01). Cultures were fed with fresh adipogenic differentiation medium every 3 to 4 days for a period of up to 2 weeks. Cells were then fixed in 10% neutral buffered formalin and rinsed with PBS. Adipogenic differentiation was determined by staining for fat globules with oil red O (Sigma).

Chondrogenesis: Confluent cultures of primary ASCs were induced to undergo chondrogenesis by replacing the stromal medium with chondrogenic induction medium (STEMPRO® Chondrogenesis Differentiation Kit (Thermo-Fisher Scientific, previously Invitrogen), a kit used for the chondrogenic differentiation of mesenchymal stem cells in tissue culture vessels that contains STEMPRO® Chondrocyte Differentiation Basal Medium (Gibco® Cat. # A10069) and STEMPRO® Chondrogenesis Supplement (Gibco® Cat. # A10064-01). Cultures were fed with fresh chondrogenic induction medium every 3 to 4 days for a period of up to 3 weeks. Cells were then fixed in 10% neutral buffered formalin and rinsed with PBS. Chondrogenic differentiation was determined by staining for proteoglycans with Alcian blue (Sigma).

Final Product Characterization

Figure 4:
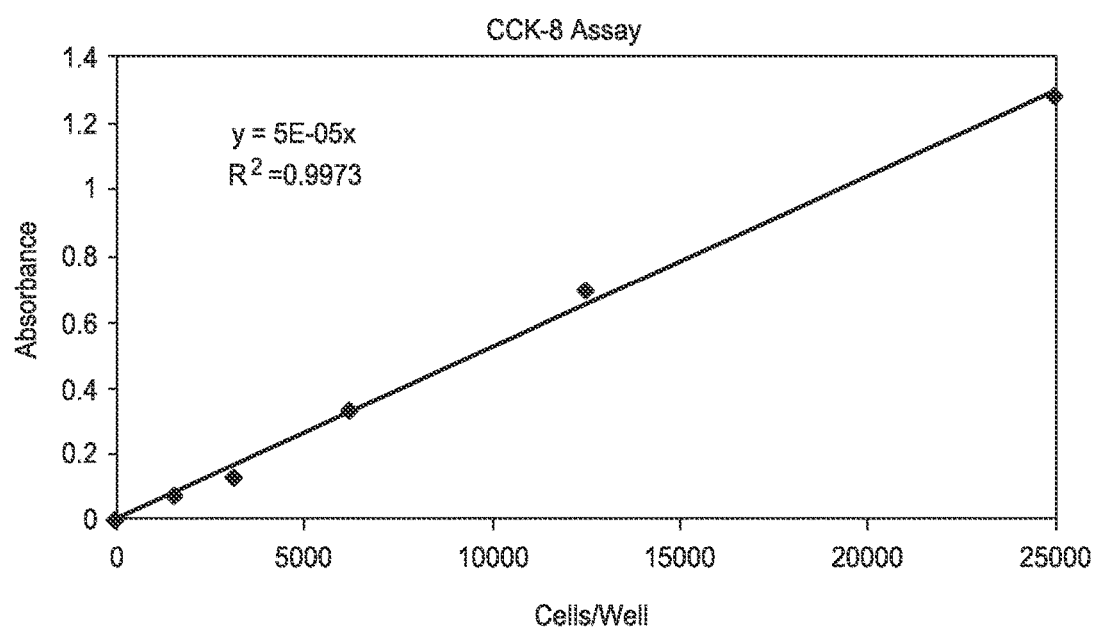
FIG. 4 illustrates a standard curve of total live ASCs using the CCK-8 assay.

Cell count may be preformed [sic] with a CCK-8 Assay. Cell Counting Kit 8 (CCK-8, Dojindo Molecular Technologies, Maryland) allows sensitive colorimetric assays for the determination of the number of viable cells in cell proliferation assays. With reference to FIG. 4, there is illustrated a standard curve of total live ASCs using the CCK-8 assay. WST-8 [2-(2-methoxy-4-nitrophenyl)-3-(4-nitrophenyl)-5-(2,4-disulfophenyl)-2H-tetrazolium, monosodium salt] is reduced by dehydrogenases in cells to give a yellow colored product (formazan), which is soluble in the tissue culture medium. The amount of the formazan dye generated by the activity of dehydrogenases in cells is directly proportional to the number of living cells. The allografts were thawed and rinsed with PBS and then patted dry. Growth medium and CCK-8 solution were added into the allografts at a ratio of 10:1 cultured at 37° C. for 2 hours and evaluated in a plate reader with excitation set to 460 nm and emission set to 650 nm. The results were interpolated from a standard curve (FIG. 4) based on ASCs only (passage=3).

Histology

When the cultures were terminated, the constructs were fixed in 10% neutral buffered formal in (Sigma, St. Louis, Mo.) for 48 h, put in a processor (Citadel 2000; Thermo Shandon, Pittsburgh, Pa.) overnight, and embedded in paraffin. Sections were cut to 8 μm and mounted onto glass slides and stained with hematoxylin and eosin (H&E). Conventional light microscopy was used to analyze sections for matrix and cell morphology.

Statistical Analysis

All quantitative data were expressed as the mean±standard deviation. Statistical analysis was performed with one-way analysis of variance. A value of p<0.05 was considered statistically significant.

Results

Final Product Appearance

FIGS. 3A-3D illustrate an appearance of strips, dowels and disks. In these embodiments, all have a cortical bottom and cancellous top. Other embodiments may be used.

ASC Characterization

Flow Cytometry—Immunophenotype of SVF

The SVF were stained with CD105, CD90 and CD73 to determine if there were significant numbers of MSC present. The immunophenotype of the stromal vascular fraction was consistent from donor to donor. The large cells (mean 3%) have the following immunophenotype and mean percentage: D7-FIB+ (36%), CD105+ (43%), CD90+(63%), CD73+ (28%) and CD34+ (62%). The small cells (mean 97%) contain only a small percentage of the markers tested and therefore could not be immunophenotyped with this method: D7-FIB (5%), CD105 (6%), CD90 (15%), CD73 (6%) and CD34 (10%). The SVF contained a significant population of CD34+ cells (Large CDC34+ 62% and small CD34+ 10%). The paucity of CD45+ cells (Large 15% and small 3%) would suggest that the SVF does not contain significant numbers of WBC (CD45+, low FSC, low SSC) or hematopoietic stem cells (CD34+, low CD45+, medium FSC, low SSC). The anti-Fibroblasts/Epithelial Cells (clone D7-FIB) antibody has been reported to be a good marker for MSC. The large cells were D7-FIB+36% and the small cells were D7-FIB+5%. CD271 should be negative on SVF cells and the large cells were CD271+10% and the small cells were CD271+0%. Following adherence of the SVF (ASCs, P1), the immunophenotype became more homogenous for both the large and small cells. The large cells (53%) have the following immunophenotype and percentage: D7-FIB+ (93%), CD105+(98%), CD90+(96%) and CD73+(99%). The small cells (47%) have the following immunophenotype and percentage: D7-FIB+(77%), CD105+(75%), CD90+ (58%) and CD73+(83%). The ASCs has lost CD34 marker expression (P3: large 4% and small 1%) (P1: large 8% and small 6%) and the CD45+ cells remained low (P3: large 2% and small 2%) (P1: large 3% and small 1%). This would suggest that there are few WBC (CD45+, low FSC, low SSC) or hematopoietic stem cells (CD34+, low CD45+, medium FSC, low SSC) present. The anti-Fibroblasts/Epithelial Cell (clone D7-FIB) antibody for the adherent and cultured cells showed an increased expression. The large cells were D7-FIB+93% and the small cells were D7-FIB+ 77%. CD271 should become positive following adherence and culture of the SVF. For P3 the large cells were CD271+ 4% and the small cells were CD271+1%. For P1 the large cells were CD271+27% and the small cells were CD271+ 3%. CD271 does not seem to be a useful marker for cultured MSC but more data is required.

Estimated Mean Total Percentage of MSC

CD105 was chosen to estimate the mean total percentage of MSC; although there is no single surface marker that can discern MSC in a mixed population. For the SVF with a mean of 3% large cells, a mean of 43% CD105+ cells, the mean total percentage would be 1.3%. For the SVF with a mean of 98% small cells, a mean of 6% CD105+ cells, the mean total percentage would be 5.9%. Combining the large and small totals gives a mean total of 7.2% MSC for the SVF.

In Vitro Tri-Lineage Differentiation

Figure 5:
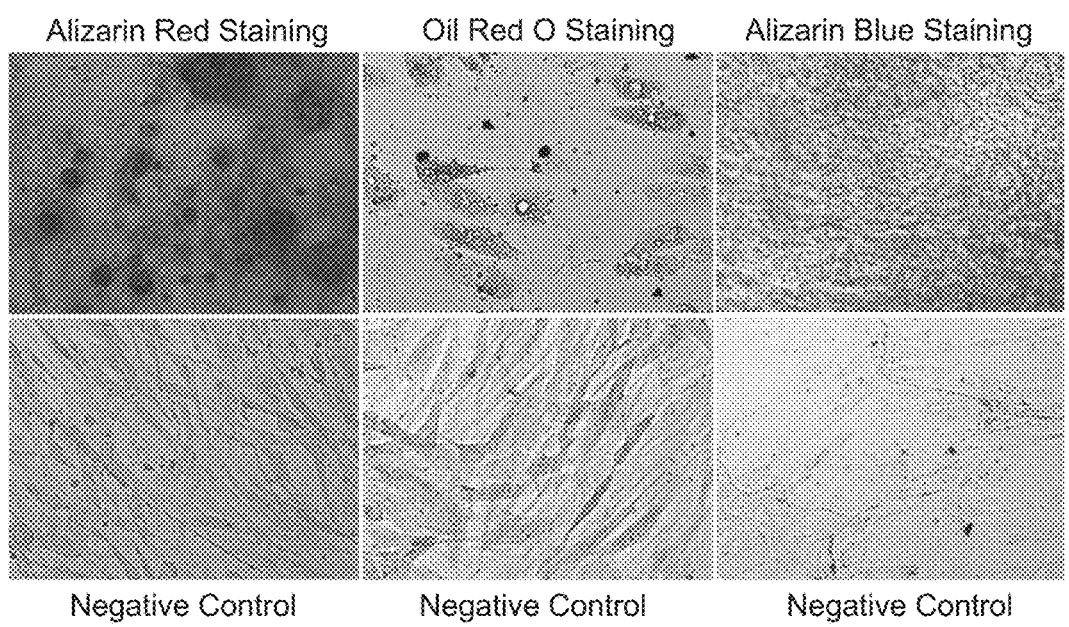
FIG. 5 illustrates mineral deposition by ASCs cultured in osteogenic medium (images shown at 20× magnification)

FIG. 5 illustrates mineral deposition by ASCs cultured in osteogenic medium (A) indicating early stages of bone formation. The samples were stained with alizarin red S. Negative control (D) showed no sign of bone formation. Fat globules seen in ASCs cultured in adipogenic medium (B) indicating differentiation into adipocytes. The samples were stained with Oil red O. The picture (E) is negative control. Proteoglycans produced by ASCs cultured in chondrogenic medium (C) indicating early stages of chondrogenesis. The samples were stained with alcian blue. The negative control (F) showed no sign of chondrogenesis.

For the osteogenic differentiation, morphological changes appeared during the second week of the culture. At the end of the 21-day induction period, some calcium crystals were clearly visible. Cell differentiation was confirmed by alizarin red staining (FIG. 5 image (A)).

The adipogenic potential was assessed by induction of confluent ASCs. At the end of the induction cycles (7 to 14 days), a consistent cell vacuolation was evident in the induced cells. Vacuoles brightly stained for fatty acid with oil red O staining (FIG. 5 image (B)). Chondrogenic potential was assessed by induction of confluent ASCs. At the end of the induction cycles (14 to 21 days), the induced cells were clearly different from non-induced control cells. Cell differentiation was confirmed with Alcian blue staining (FIG. 5 image (C)).

Final Product Characterization

Cell Count: CCK-8 Assay 28 grafts were tested from 8 donors and had an average of 50,000 live cells/graft.

Histology

Figure 6:
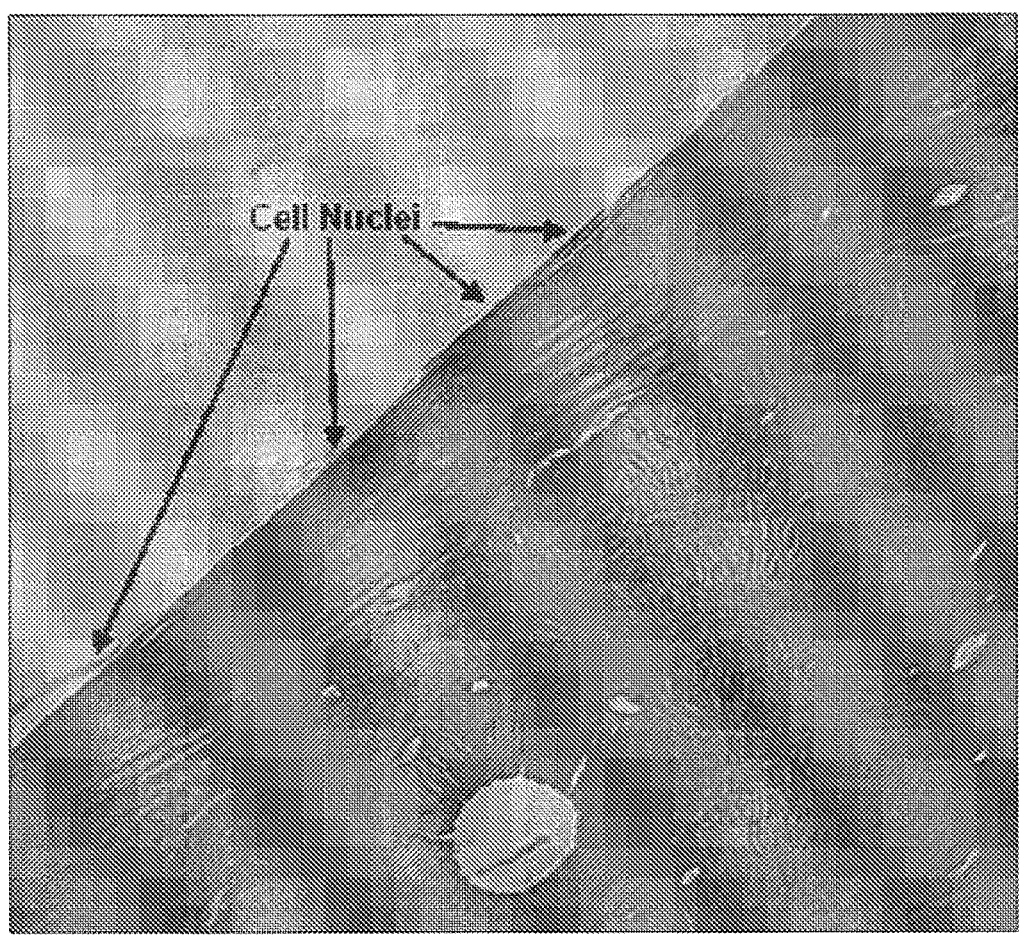
FIG. 6 illustrates H&E staining showed that cells adhered to the bone surface.

H&E was performed to demonstrate cell morphology in relation to the underlying substrate (cancellous bone matrix). The stem cells are elongated and adhere to the surface of cancellous bone. FIG. 6 is an illustration of H&E staining that showed that stem cells adhered to the bone surface.

CONCLUSIONS

The ability of DBM to enhance osteogenesis of ASCs in vitro and in vivo is believed to be due to the interaction of osteoprogenitors with these matrix incorporated osteoinductive factors, which can induce MSCs into osteoblasts. In turn, the incorporation of an osteogenic cell source into DBM can potentially limit the need for the migration and expansion of indigenous osteoprogenitors within defect sites, allowing for an increased rate of bone formation and osseointegration. See, for example, the following, which are incorporated by reference:

Liu, G., et al., *Evaluation of partially demineralized osteoporotic cancellous bone matrix combined with human bone marrow stromal cells for tissue engineering: an in vitro and in vivo study*. Calcif Tissue Int, 2008. 83(3): p. 176-85.

Wang, J. and M. J. Glimcher, *Characterization of matrix-induced osteogenesis in rat calvarial bone defects: II. Origins of bone forming cells*. Calcif Tissue Int, 1999. 65(6): p. 486-93.

Wang, J. and M. J. Glimcher, *Characterization of matrix-induced osteogenesis in rat calvarial bone defects: I. Differences in the cellular response to demineralized bone matrix implanted in calvarial defects and insubcutaneous sites*. Calcif Tissue Int, 1999. 65(2): p. 156-65.

Wang, J., et al., *Characterization of demineralized bone matrix-induced osteogenesis in rat calvarial bone defects: III. Gene and protein expression*. Calcif Tissue Int, 2000. 67(4): p. 314-20.

Bruder, S. P. and B. S. Fox, *Tissue engineering of bone. Cell based strategies*. Clin Orthop Relat Res, 1999(367 Suppl): p. S68-83.

Many studies have demonstrated that purified, culture-expanded human MSCs can be directed into the osteogenic lineage in vitro, culminating in a mineralized matrix production. See, for example, the following, which are incorporated by reference:

Chen, L. Q., et al., [*Study of MSCs in vitro cultured on demineralized bone matrix of mongrel*]. Shanghai Kou Qiang Yi Xue, 2007. 16(3): p. 255-8.

Honsawek, S., D. Dhitiseith, and V. Phupong, *Effects of demineralized bone matrix on proliferation and osteogenic differentiation of mesenchymal stem cells from human umbilical cord*. J Med Assoc Thai, 2006. 89 Suppl 3: p. 8189-95.

Kasten, P., et al., *Ectopic bone formation associated with mesenchymal stem cells in a resorbable calcium deficient hydroxyapatite carrier*. Biomaterials, 2005. 26(29): p. 5879-89.

Qian, Y., Z. Shen, and Z. Zhang, [*Reconstruction of bone using tissue engineering and nanoscale technology*]. Zhongguo Xiu Fu Chong Jian Wai Ke Za Zhi, 2006. 20(5): p. 560-4.

Liu, G., et al., *Tissue-engineered bone formation with cryopreserved human bone marrow mesenchymal stem cells*. Cryobiology, 2008. 56(3): p. 209-15.

Ko, E. K., et al., *In vitro osteogenic differentiation of human mesenchymal stem cells and in vivo bone formation in composite nanofiber meshes*. Tissue Eng Part A, 2008. 14(12): p. 2105-19.

The ability to mineralize the extracellular matrix and to generate bone is not unique to MSCs. In fact, ASCs possess a similar ability to differentiate into osteoblasts under similar conditions. Human ASCs offer a unique advantage in contrast to other cell sources. The multipotent characteristics of ASCs, as wells as their abundance in the human body, make these cells a popular source in tissue engineering applications. This consistent cell-based new product has the potential to be effective for bone regeneration.

What is claimed is:

1. A method of making an allograft product for enhancing bone formation, the method consisting of:
   providing a bone substrate obtained from a human, cadaveric donor;
   providing a tissue comprising mesenchymal stem cells and unwanted cells from the human, cadaveric donor;
   processing the tissue to form a cell suspension comprising the mesenchymal stem cells and the unwanted cells;
   adding the cell suspension to the bone substrate to form a seeded bone substrate;
   incubating the seeded bone substrate for a period of time to allow the mesenchymal stem cells to adhere to the bone substrate; and
   rinsing the seeded bone substrate to remove the unwanted cells from the bone substrate;
   thereby making the allograft product for enhancing bone formation, wherein the allograft product comprises bone substrate with mesenchymal stem cells adhered thereto.

2. The method in accordance with claim 1, wherein the tissue is selected from the group consisting of adipose tissue, muscle tissue, and bone marrow tissue.

3. A method in accordance with claim 1, wherein the bone substrate comprises bone tissue that has been subjected to a demineralization process.

4. A method in accordance with claim 1, wherein the bone substrate comprises cortical bone.

5. A method in accordance with claim 1, wherein the bone substrate comprises cancellous bone.

6. A method in accordance with claim 1, wherein the bone substrate comprises ground bone.

7. A method in accordance with claim 1, wherein the bone substrate comprises both cortical and cancellous bone.

8. A method in accordance with claim 1, wherein the bone substrate comprises demineralized cancellous bone.

9. A method in accordance with claim 1, wherein the bone substrate comprises fully demineralized bone, partially demineralized bone, or a combination thereof.

10. A method in accordance with claim 1, wherein the incubating is performed for about 1-3 days.

11. A method in accordance with claim 1, wherein the incubating is performed for no more than about 3 days.

12. A method in accordance with claim 1, wherein the incubating consists of incubating the seeded bone substrate in growth medium.

13. A method of making an allograft product for enhancing bone formation, the method consisting of:
providing a bone substrate obtained from a human, cadaveric donor;
providing a tissue comprising mesenchymal stem cells and unwanted cells from the human, cadaveric donor;
processing the tissue to form a cell suspension comprising the mesenchymal stem cells and the unwanted cells;
adding the cell suspension to the bone substrate to form a seeded bone substrate;
incubating the seeded bone substrate for a period of time to allow the mesenchymal stem cells to adhere to the bone substrate;
rinsing the seeded bone substrate to remove the unwanted cells from the bone substrate; and
placing the seeded bone substrate into a cryopreservation medium;
thereby making the allograft product for enhancing bone formation, wherein the allograft product comprises bone substrate with mesenchymal stem cells adhered thereto.

14. The method in accordance with claim 13, wherein the tissue is selected from the group consisting of adipose tissue, muscle tissue, and bone marrow tissue.

15. A method in accordance with claim 13, wherein the bone substrate comprises bone tissue that has been subjected to a demineralization process.

16. A method in accordance with claim 13, wherein the bone substrate comprises cortical bone.

17. A method in accordance with claim 13, wherein the bone substrate comprises cancellous bone.

18. A method in accordance with claim 13, wherein the bone substrate comprises ground bone.

19. A method in accordance with claim 13, wherein the bone substrate comprises both cortical and cancellous bone.

20. A method in accordance with claim 13, wherein the bone substrate comprises demineralized cancellous bone.

21. A method in accordance with claim 13, wherein the bone substrate comprises fully demineralized bone, partially demineralized bone, or a combination thereof.

22. A method in accordance with claim 13, wherein the incubating is performed for about 1-3 days.

23. A method in accordance with claim 13, wherein the incubating is performed for no more than about 3 days.

24. A method in accordance with claim 13, wherein the incubating consists of incubating the seeded bone substrate in growth medium.

* * * * *